United States Patent [19]
Cook et al.

[11] Patent Number: 6,143,490
[45] Date of Patent: *Nov. 7, 2000

[54] TREATING BLOOD OR BLOOD PRODUCT WITH A COMPOUND HAVING A MUSTARD AND A NUCLEIC ACID BINDING MOIETY

[75] Inventors: David Cook; Susan Wollowitz, both of Walnut Creek; Aileen Nerio, Santa Clara, all of Calif.

[73] Assignee: Cerus Corporation, Concord, Calif.

[ * ] Notice: This patent is subject to a terminal disclaimer.

[21] Appl. No.: 08/476,842

[22] Filed: Jun. 7, 1995

Related U.S. Application Data

[63] Continuation-in-part of application No. 08/338,040, Nov. 14, 1994, Pat. No. 5,691,132.

[51] Int. Cl.$^7$ .............................. A01N 1/02; C12N 7/06
[52] U.S. Cl. ............................................... 435/2; 435/238
[58] Field of Search ........................................ 435/2, 238

[56] References Cited

U.S. PATENT DOCUMENTS

| | | | |
|---|---|---|---|
| 3,819,270 | 6/1974 | Hirschfeld | 356/39 |
| 4,107,182 | 8/1978 | Liebman et al. | 260/343.21 |
| 4,124,598 | 11/1978 | Hearst et al. | 260/343.2 |
| 4,147,703 | 4/1979 | Liebman et al. | 260/343.21 |
| 4,150,042 | 4/1979 | Liebman et al. | 260/346.22 |
| 4,182,750 | 1/1980 | Sullivan et al. | 424/1 |
| 4,196,281 | 4/1980 | Hearst et al. | 536/28 |
| 4,252,653 | 2/1981 | Beck et al. | 210/321.3 |
| 4,269,851 | 5/1981 | Kaufman | 424/279 |
| 4,269,852 | 5/1981 | Kaufman | 424/279 |
| 4,294,822 | 10/1981 | Kaufman | 424/59 |
| 4,298,614 | 11/1981 | Kaufman | 424/279 |
| 4,370,344 | 1/1983 | Kaufman | 424/279 |
| 4,683,195 | 7/1987 | Mullis | 435/91 |
| 4,683,202 | 7/1987 | Mullis | 435/91 |
| 4,727,027 | 2/1988 | Wiesehahn et al. | 435/173 |
| 4,748,120 | 5/1988 | Wiesehahn | 435/173 |
| 4,970,230 | 11/1990 | Goupil | 514/455 |
| 5,055,485 | 10/1991 | Geacintov et al. | |
| 5,399,719 | 3/1995 | Wollowitz et al. | 549/282 |
| 5,473,083 | 12/1995 | Heindel et al. | 549/280 |

FOREIGN PATENT DOCUMENTS

| | | |
|---|---|---|
| 0 111 418 A2 | 6/1984 | European Pat. Off. . |
| WO 96/39818 | 12/1996 | WIPO . |
| WO 97/07674 | 3/1997 | WIPO . |
| WO 98/51660 | 11/1998 | WIPO . |

OTHER PUBLICATIONS

Heaton et al., British J. Haematology 57(3):467–78 (1984).
Shooter et al., "Assays for phosphotriester formation in the reaction of bacteriophage R17 with a group of alkylating agents", Chemico–Biological Interactions 11 (6) : 575–88 (1975).
Lawley et al., "Inactivation of bacteriophage T7 by mono–and difunctional sulfur mustards in relation of cross–linking and depurination of bacteriophage DNA", J. Molecular Biology 39 (1) : 181–98 (1969).
Rytir et al. (1974). "A study on the effect of certain compounds during elimination of plasmids in *Escherichia coli*" *Folia Microbiol.* 20:17–23.
Resnick, et al., Human T–cell lymphotrophic viruses: Synctia Formation, JAMA 255:1887 (1986).
Update: HIV Infections in health–care workers exposed to blood of infected patients; Morbidity and Mortality Weekly Report 36:285 (1987).
Dodd, R.Y. "Will Blood Products be free of infectious agents?" *Transfusion Medicine in the 1990's* American Association Blood Banks (1990).
Surgenor, D.M. et al., Red cell transfusions in coronary artery bypass surgery (DRFs 106 and 107), Transfusion 32:458–464 (1992).
Wallace, E.L., et al, "Collection and transfusion of blood and blood components in the United States, 1989", Transfusion 33:139–144 (1993).
"How Safe Is Our Blood", U.S. News and World Report, Jun. 27, 1994, 68–78.
Hilfenhaus, J., et al., "A strategy for testing established human plasma protein manufacturing procedures for the ability to inactivate or eliminate human immunodeficiency virus" J. Bio. Stand 15:251–263 (1987).
Horowitz, B., et al., "Inactivation of viruses in labile blood derivatives" Transfusion 25:516–522 (1985).
Moroff, G., et al, "The influence of irradiation on stored platelets" Transufion 25:453–456 (1986).
Proudouz, K.N., et al., "Use of Laser–UV for inactivation of virus in blood products", Blood vol. 70:2 pp. 589–592, (1987).
Wagner, S.J., et al., "Red cell alterations associated with virucidal methylene blue phototreatment", Transfusion 33:30–36 (1993).
Bruisten, S.M., et al., "Efficiency of white cell filtration and a freeze–thaw procedure for removal of HIV–infected cells from blood", Transfusion 30:833 (1990).
Winslow, R.M., "Red cell substitutes: Current status, 1992" Nance, S.M., editor, Blood Safety: Current Challenges AABB p. 151–167 (1992).
Peck, R.M. et al., "Nitrogen mustard analogs of antimalarial drugs", J. Am. Chem. Soc. 81 3984–9 (1959).
Gravitt, G.L., et al., "DNA–directed alkylating agents. 4. 4–anilinoquinoline–based minor groove directed aniline mustards" J. Med. Chem 34:1552–1560 (1991).

(List continued on next page.)

*Primary Examiner*—Sandra E. Saucier
*Attorney, Agent, or Firm*—Morrison & Foerster LLP

[57] ABSTRACT

Methods and compositions for treating pathogens in material are described, including methods of decontaminating human fluids prior to processing in the clinical laboratory and methods for decontaminating blood products prior to in vivo use. The techniques handle large volumes of human serum without impairing the testing results. Novel compounds for photodecontaminating biological material are also contemplated which are compatible with clinical testing, in that they do not interfere with serum analytes.

21 Claims, 9 Drawing Sheets

OTHER PUBLICATIONS

Cummings, J., et al., "Determination of reactive nitrogen mustard anti–cancer drugs in plasma by high–performance liquid chromatography using derivatization", Anal. Chem. 63:1514 (1991).

Maron, D.M., et al., "Revised methods for the salmonella mutagenicity test" Mutation Research 113:173–215 (1983).

Lin, L., et al., "Use of 8–Metboxypsoralen and long–wavelength ultraviolet radiation for decontamination of platelet concentrates" Blood 74:1 pp. 517–525 (1989).

Ganem, D., et al., "The molecular biology of the Hepatitis B viruses" Ann. Rev. Biochem. 56:651–93 (1987).

Hanson, C.V., et al, "Application of a Rapid microplaque assay for determination of HIV neutralizing antibody titers", J. Clin. Microbio. 28:9 pp. 2030–2034 (1990).

Preston, R.K. et al., "Further investigations of heterocyclic alkylating agents", J.Med. Chem. 7:471–80 (1964).

Wilson, W.R. et al., Patent No. WO 94/27954 "Nitrobenzyl Mustard Quaternary Salts and their use as Hypoxia–selective cytotoxic agents", Filing date May 24, 1994.

LoGrippo, G.A. et al., "Chemical and combined methods for plasma sterilization", 6th Congress of the International Society of Blood Transfusion; Hollander, editor pp. 225–230 (1958).

Mattes, W.B., et al., "GC–rich regions in genomes as target for DNA alkylation", Carcinogenesis vol. 9 No. 11 pp. 2065–2072 (1988).

Prakash A.S., et al. DNA–directed alkylating ligands as potential antitumor agents: sequence specificity of alkylation by intercalating aniline mustards. Biochem. (1990);29:9799–9807.

Ferguson L.R., et al. Modulation of mutagenic properties in a series of DNA–directed alkylating agents by variation of chain length and alkylator reactivity. Mutation Res. (1992);265:181–193.

Hartley J.A., et al. Effect of ionic strength and cationic DNA affinity binders on the DNA sequence selective alkylation of guanine N7–positions by nitrogen mustards. Biochem. (1990);29:2985–2991.

Gourdie T.A., et al. Synthesis and evaluation of DNA–targeted spatially separated bis(aniline mustards) as potential alkylating agents with enhanced DNA cross–linking capability. J. Med. Chem (1991);34:240–248.

Valu K.K., et al. DNA–directed alkylating agents. 3. structure–activity relationships for acridine–linked aniline mustards: consequences of varying the length of the linker chain. J. Med. Chem. (1990);33:3014–3019.

Gourdie T.A., et al. DNA–directed alkylating agents. 1. structure–activity relationships for acridine–linked aniline mustards: consequences of varying the reactivity of the mustard. J. Med. Chem (1990);33:1177–1186.

Panthananickal A., et al. Structure–activity relationships in antitumor aniline mustards. J. of Med. Chem. (1978);21(1):16–26.

Sunters A., et al. The cytotoxicity, DNA crosslinking ability and DNA sequence selectivity of the aniline mustards melphalan, chlorambucil and 4–[BIS(2–chloroethyl)amino] benzoic acid. Biochem. (1992);44(1):59–64.

Fraser M.J., et al. Inactivation of bacteriophage ^ and ^ DNA by nitrogen mustard. Mut. Res. (1982);96;153–165.

Fox M., et al. The genetic toxicology of nitrogen and sulphur mustard. Mut. Res. (1980);75:131–168.

Millard J.T., et al. Diepoxybutane cross–links DNA at 5'–GNC sequences. Biochem. (1993);32:2120–2124.

Charache S., et al. Evaluation of extracorporeal alkylation of red cells as a potential treatment for sickle cell anemia. Blood (1976);47(3):481–488.

Antonello C., et al. Diethylaminoalkyloxycoumarin and Furocoumarin Derivatives. Il Farmaco—Ed. Sc. (1979); 34:139–156.

Friedman et al., "Viral inactivation and reduction in cellular blood products" Rev. Fr. Transfus. Hemobiol. (1993) 36: 83–91.

Krowicki, K. et al., "Novel DNA groove binding alkyiators: design synthesis, and biological evaluation" J. Med. Chem. (1988) 31:341–345.

Wagner, S.J. et al. "Approaches to the reduction of viral infectivity in cellular blood components and single donor plasma" Transfusion Medicine Reviews (1991) 5 (1): 18–32.

Budowsky et al., "Principles of selective inactivation of the viral genome: Dependence of the rate of viral RNA modification on the number of protonizable groups in ethyleneimine oligomers" Vaccine Res. (1996) 5:29–39.

Cates et al., "Phosphorus–nitrogen compounds. 24. Phosphoramide mustard carrier derivatives" J. Med. Chem. (1984) 27:397–401.

Heaton et al., "Use of Adsol® preservation solution for prolonged storage of low viscosity AS–1 red blood cells" Brit. J. Haematol. (1984) 57:467–478.

Kohn et al., "Synthesis and DNA–squence selectivity of a series of mono– and difunctional 9–aminoacridine nitrogen mustards" J. Med. Chem. (1994) 37:67–72.

Kostyanovskii et al., "Oligomers of aziridines and N–β–aziridinoethylamides" Bulletin of the Academy of Sciences of the USSR, Division of Chamical Science (1988) 37:2315–2323.

Kyvsgaard et al., "Activity of antibodies against Salmonella dublin, Toxoplasma gondii, or Aetinobacillus pleuropneumoniae in sera after treatment with electron beam irradiation or binary ethylenimine" Clin. Diag. Lab. Immunol. (1996) 3:628–634.

Hartman et al, Four–Year Study Concerning the Inactivation of Viruses in Blood and Plasma, vol. 28, No. 2, p. 244–256 (Presented at the 55th Annual Meeting of the American Gastroenterological Association, San Francisco, California, Jun. 1954.).

Kelly et al., American Society for Experimental Pathology 10:361–362 (1951).

Kelly et al. American Society for Experimental Pathology 9:335–336 (1950).

Berman, Chem Abstracts 99:205685t (1983).

Davis, Chem Abstracts 113:536f (1990).

Drake et al., "Effect of Nitrogen Mustard on Virus of Serum Hepatitis in Whole Blood," P Soc Exp Biol Med, 80:310–313 (1952).

Glaz, Chem Abstracts 79:73648h (1973).

Hammond, Chem Abstracts 103:171499u (1985).

Hartman et al., "On the Chemical Sterilization of Blood and Blood Plasma," Proc of Society of Exp Biology and Medicine, 70:248–254 (1949).

Hartman et al., "Preparation and Sterilization of Blood Plasma," Am J Clin Pathol, 24:339–348 (1954).

Creech, H.J. et al., (Jan. 1, 1972) "Anitumor and mutagenic properties of a variety of heterocyclic nitrogen and sulfur mustards" Journal of Medicinal Chemistry 15(7):739–746.

TREATING BLOOD OR BLOOD PRODUCT WITH A COMPOUND HAVING A MUSTARD AND A NUCLEIC ACID BINDING MOIETY

This application is a continuation in part of U.S. patent application Ser. No. 08/338,040, filed Nov. 14, 1994, now U.S. Pat. No. 5,691,132.

FIELD OF THE INVENTION

The invention generally relates to new compounds and methods for the in vitro inactivation of pathogens in biological material intended for in vitro or in vivo use, and in particular the inactivation of pathogens in solutions containing red blood cells, prior to clinical testing or transfusion.

BACKGROUND

The presence of pathogens in blood products, as well as other biological materials, is recognized as a significant health problem to health workers as well as recipients of the materials.

With regard to health workers, a great volume of human fluids is handled daily as part of the routine monitoring of hospital patients by obtaining and testing human fluids (blood, urine, spinal fluid, etc.). Typically, each admitted patient has at least a tube of blood collected every day by a phlebotomist. During the transferring, portioning and testing process, each sample tube is handled by a clinical worker while its contents are exposed. This intensive handling of potentially infectious human fluids is not without health risk. The Occupational Safety and Health Administration (OSHA) estimates that over five million health workers, including hospital laboratory workers, are exposed to blood borne-pathogen infections in the work place annually. The pathogen responsible for the overwhelming majority of infections is the hepatitis B virus (HBV). The Center for Disease Control (CDC) estimates there are twelve thousand cases of HBV infection among health workers each year. Of these cases, over five hundred require hospitalization and approximately two hundred and fifty of these patients die (i.e. from fulminant hepatitis, cirrhosis or liver cancer). See *Guidelines for Prevention of Transmission of HIV and HBV to Health-Care and Public Safety Workers*, CDC (February 1989). Most full time laboratory employees contract hepatitis at least once during their career. Indeed, up to one third of all health care workers show serological evidence of a previous HBV infection. Id.

Following the recognition of Acquired Immunodeficiency Syndrome (AIDS), clinical laboratories have instituted additional precautions. For example, rather than using manually positioned plastic inserts to maintain the separation of cells from serum after samples are centrifuged, a "gel" is now available that is in the empty tube at the time the blood is drawn. When the tube is centrifuged the cells go below the gel while the serum remains above. While the separation can be maintained in this manner without as much sample handling, this does not reduce the handling of the technologist at the point of analysis. Unfortunately, an infectious virus can persist in a liquid or dried state for prolonged periods of time, possibly even at elevated temperatures. Resnick et al., JAMA 255:1887 (1986).

Preventative measures such as gloves and eye-wear are not complete solutions to the problem. Accidents in the laboratory or clinic typically involve exposure over a larger portion of the body and disease can be transmitted through the skin and mucous membranes. Morbidity and Mortality Weekly Report 36:285 (1987).

Clearly, there remains a need for a more adequate solution to blood borne-pathogen infections in the work place. Such a solution should serve as a protection against a wide range of pathogens. Furthermore, the mechanics of the solution should not unduly interfere with operations of a laboratory or blood bank.

Another significant problem is the contamination of the blood supply for in vivo use. The safety of the blood supply continues to be threatened by the transmission of pathogens by transfusion. While the threat posed by the human immunodeficiency virus (HIV) and the Acquired Immune Deficiency Syndrome (AIDS) is now widely publicized, contamination of blood products with a number of other blood-borne infectious viral agents is of even greater concern. See R. Y. Dodd, In: *Transfusion Medicine in the 1990's* (American Assoc. Blood Banks 1990) (S. J. Nance, ed.). For example, in the United States, it is estimated that up to ten (10) percent of multiply transfused recipients develop hepatitis accounting for many thousands of cases annually.

Whole blood collected from volunteer donors for transfusion recipients is typically separated into its components: red blood cells, platelets, and plasma. Each of these fractions are individually stored and used to treat a multiplicity of specific conditions and disease states.

The red blood cell component is used primarily to treat trauma, chronic anemia, and blood loss due to surgery (particularly cardiac and liver surgery), including postoperative bleeding. D. M. Surgenor et al. Transfusion 32:458 (1992). Approximately twelve (12) million units of red cells are transfused into approximately four (4) million recipients annually in the United States alone. E. L. Wallace et al. Transfusion 33:139 (1993).

The safety of the blood supply cannot be assured by merely testing the blood for pathogens before transfusion. Most testing relies on the detection of antibodies to the pathogen in the prospective blood donor. It is now well-documented that infectious agents can be transmitted by "seronegative" blood donors, i.e. donors that have no detectable antibodies to the pathogen. For example, thirteen cases of transfusion-related AIDS have been reported to the Centers for Disease Control (CDC) among recipients of blood that was pre-tested and found negative for antibody to the HIV-1 virus.

Clerical errors and other mistakes further expose patients to contaminated, incorrectly tested or mislabeled blood. To complicate the problem, one bad unit can create several victims, since whole blood is routinely split into components. Mistakes are not infrequent in blood banks. Since the beginning of 1990, 29,586 blood bank errors and accidents have been reported to the FDA. "How Safe Is Our Blood," U.S. News and World Report, Jun. 27, 1994, 68–78. Recalls by blood centers of blood released in error are generally ineffective because they take place months or years after the blood products have been transfused.

An alternative approach to eliminate transmission of diseases through blood products is to develop a means to inactivate pathogens in transfusion products. Some of these techniques such as heat [J. Hilfenhous et al. J. Biol. Std. 70:589 (1987)], solvent/detergent treatment [B. Horowitz et al. Transfusion 25:516 (1985)], gama-irradiation [G. Moroff et al. Transfusion 26:453 (1986)] or UV alone [K. N. Proudouz et al. Blood 70:589 (1987)] are completely incompatible with maintenance of red cell function.

Another means to inactivate pathogens is the use of methylene blue. S. J. Wagner et al. examined methylene blue as a virucidal for red cell solutions. S. J. Wagner et al.

Transfusion 33:30 (1993). Photo treatment of red cells with methylene blue was found to cause loss of ATP, enhanced ion permeability, and binding of autologous immunoglobulin (IgG) to the red cell surface. It was speculated that some general (and undesirable) modification of the red cell membrane occurs as a result of the treatment.

Yet another approach is to deplete the red cell product of contaminating lymphocytes which may harbor viral pathogens. Both leukodepletion with filters and freeze/thaw procedures have been examined. S. M. Bruisten et al. Transfusion 30:833 (1990). Complete removal of lymphocytes, however, cannot be achieved with such methods. Furthermore, leukodepletion does not address cell-free virus. Thus, this approach is not sufficient to render blood completely safe.

Finally, there is the approach of avoiding blood and using blood substitutes. Hemoglobin solutions, perfluorocarbon emulsions and vesicle-encapsulated hemoglobin have all been suggested as candidates. Unfortunately, each of these has been shown to be inadequate as a general substitute. See R. M. Winslow In: *Blood Safety: Current Challenges* (S. J. Nance ed.) (AABB 1992) (pp. 151–167).

In sum, there is a need for a means of inactivating viral pathogens in red blood cell solutions. This approach must be effective without causing harm to the blood product or the transfusion recipient.

SUMMARY OF THE INVENTION

The present invention generally relates to new compounds and methods for the in vitro inactivation of pathogens in biological material intended for in vitro or in vivo use, and in particular the inactivation of pathogens in solutions containing red blood cells, prior to clinical testing or transfusion. In accordance with the present invention, a compound having a nucleic acid binding ligand and a mustard group is selectively employed to treat contamination by nucleic acid-containing microorganisms, including pathogenic viruses. Without intending to suggest a mechanism for the present invention, such compounds are alkylating agents.

The present invention contemplates a method of decontaminating pathogens in a blood product, comprising: adding a compound having a mustard group and a nucleic acid binding ligand comprising a psoralen group or an acridine group to a biological composition suspected of containing pathogens, to create a mixture, said compound reaching a final concentration sufficient to inactivate substantially all of said pathogens, and incubating said mixture without significant damage to said biological composition. In one embodiment, the compound is added to the biological composition to a final concentration of said compound of between 1 $\mu$g/ml and 250 $\mu$g/ml. In another embodiment, the mixture is incubated for between 1 minute and 48 hours. In an embodiment of the present invention, the compound is added to the biological composition, the compound is in a mixture comprising dextrose, sodium chloride, mannitol, adenine and $H_2O$.

The present invention contemplates that the biological composition comprises a blood product. The present invention also contemplates an additional step: c) transfusing said blood product into a mammal. In one embodiment, the blood product transfused comprises red blood cells, or specifically, red blood cell concentrate.

The present invention contemplates the inactivation of both viral and bacterial pathogens. Compounds contemplated by the present invention for this method are 8-[3-(Bis-2-chloroethyl) amino]propyloxypsoralen or 8-[N,N-Bis-(2-chloroethyl)-3-aminopropoxy]psoralen 5-[3-Bis-2-chloroethy) aminopropyly]methy-8-methoxypsoralin or 5-[N,N-Bis-(2-chloroethyl)-3-aminopropoxy]methyl-8-methoxypsoralen. 5'-[4-(Bis-2-chloroethyl)-amino-1-butylaminomethyl]-4,4',8-trimethylpsoralen, and 4'-[4-(Bis-2-chloroethyl) aminobutoxy]methyl-4,5',8-trimethylpsoralen or 4'-[4-(N,N-Bis-2-chloroethy) aminobutoxy]methyl-4,5',8-trimethylpsoralin. The invention contemplates that more than one of said compounds may be added to the biological composition. Further, the invention contemplates a step c): after incubating said mixture, removing said compound from said biological composition with an adsorbent material.

Specifically, the present invention contemplates a method of inactivating pathogens in a blood product, comprising: a) adding a compound having a mustard group and a nucleic acid binding ligand comprising a psoralen group or an acridine group to a blood product comprising red blood cells suspected of containing pathogens, to create a mixture, said compound reaching a final concentration sufficient to inactivate substantially all of said pathogens, and b) incubating said mixture for between 1 minute and 48 hours, without significant damage to said red blood cells. The compound may be added to the blood product to a final concentration of a compound having a nucleic acid binding ligand and a mustard group of between 1 $\mu$g/ml and 250 $\mu$g/ml. As an additional component, the invention contemplates that when the compound having a nucleic acid binding ligand and a mustard group is added to the blood product, the compound is in a mixture comprising dextrose, sodium chloride, mannitol, adenine and $H_2O$. In another embodiment, the method further comprises: c) transfusing said blood product into a mammal. The present invention contemplates the inactivation by this method of both viral and bacterial pathogens. Further contemplated is a blood product decontaminated by this method. Various compounds are contemplated for use in this method, including: 8-[3-(Bis-2-chloroethyl) amino]propyloxypsoralen or 8-[N,N-Bis-(2-chloroethyl)-3-aminopropoxy]psoralen, 5-[3-(Bis-2-chloroethyl) aminopropyloxy]methyl-8-methoxypsoralen or 5-[N,N,-Bis-(2-chloroethy)-3-aminopropoxy] methoxpsoralen, 5'-[4-(Bis-2-chloroethyl)-amino-1-butylaminomethyl]-4,4',8-trimethylpsoralen, and 4'-[4-(Bis-2-chloroethyl) aminobutoxy]methyl-4,5',8-trimethylpsoralen or 4'-[4-(N,N-Bis-2-chloroethyl) aminobutoxy]methyl-4,5',8-trimethylpsoralen. Further, more than one of said compounds may be added to said blood product. The present invention contemplates the additional step comprising: c) after incubating said mixture, removing said compound from said biological composition with an adsorbent material.

In yet another embodiment, the present invention contemplates compositions of matter, comprising: 8-[3-(Bis-2-chloroethyl) amino]propyloxypsoralen or 8-[N,N-Bis-(2-chloroethyl)-3-aminopropoxy]psoralen, 5-[3-(Bis-2-chloroethyl) aminopropyloxy]methyl-8-methoxypsoralen, 5-[3-(Bis-2-chloroethyl) aminopropyloxy]methyl-8-methoxypsoralen, and 4'-[4-(Bis-2-chloroethyl) aminobutoxy]methyl-4,5',8-trimethylpsoralen.

DESCRIPTION OF THE INVENTION

Figure 1:
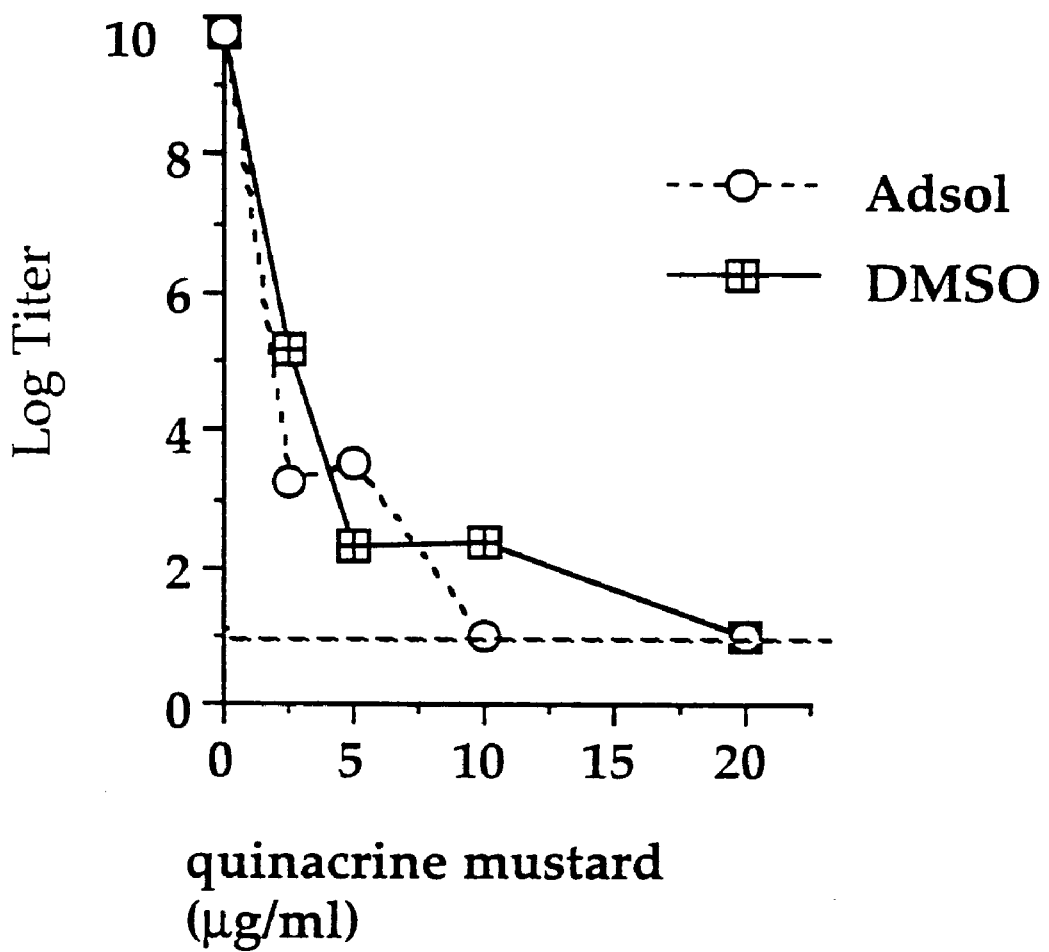
FIG. 1 is a graph showing reduction in titer of R17 treated with varying concentrations of quinacrine mustard in either Adsol or dimethyl sulphoxide (DMSO). The horizontal dotted line represents the limit of detection of the assay used.

The present invention generally relates to new compounds and methods for the in vitro inactivation of pathogens in biological material intended for in vitro or in vivo use, and in particular the inactivation of pathogens in solutions containing red blood cells, prior to clinical testing or transfusion. In accordance with the present invention, a compound having a nucleic acid binding ligand and a mustard group is selectively employed to treat contamination by nucleic acid-containing microorganisms, including pathogenic viruses and bacteria.

I. COMPOUNDS OF THE PRESENT INVENTION

Red blood cell decontamination methods using photoactivated compounds have in the past encountered a problem due to the absorbency, by hemoglobin, of light at wavelengths necessary to activate compounds. Thus, even though the previous methods would inactivate pathogens in other media, they are inefficient in the presence of red blood cells. In contrast, the present invention contemplates a method of sterilization capable of effectively inactivating pathogens even in red cell concentrates [hematocrits ranging from 1% to 60% or higher].

The present invention contemplates treating red blood cell solutions with a compound which inactivates pathogens without requiring exposure to light. The advantage of the present invention for inactivation in fluids for transfusion is two-fold. First, light is not required, allowing for a less complex technology for inactivation. Second, the decontamination compound is completely reacted after a short amount of time. The treatment is complete in several minutes or hours, depending on the compound used. Material which does not react with nucleic acids or another biomolecule hydrolyzes, leaving no compound to be transfused.

Without intending to be limited to any particular mechanism of action of the present invention, compounds of the present invention have two characteristics in common. The first characteristic is that they bind nucleic acid non-covalently. The second is that they have at least one mustard group.

A. Non-covalent Nucleic Acid Binding Group

A compound which binds nucleic acid has a "nucleic acid binding ligand", herein defined as a group which has an affinity for and can bind to nucleic acids non-covalently. There are several modes of binding to nucleic acids. Compounds which bind by any of the following modes, combinations of them, or other modes are considered nucleic acid binding ligands. While the invention is not limited to the following compounds, some examples of nucleic acid binding ligands are: a) intercalators, such as acridines, acridones, proflavin, acriflavine, actinomycins, anthracyclinones, beta-rhodomycin A, daunamycin, thiaxanthenones, miracil D, anthramycin, mitomycin, echinomycin, quinomycin, triostin, diacridines, ellipticene (including dimers, trimers and analogs), norphilin A, fluorenes and flourenones, fluorenodiamines, quinacrine, benzacridines, phenazines, phenanthradines, phenothiazines, chlorpromazine, phenoxazines, benzothiazoles, xanthenes and thioxanthenes, anthraquinones, anthrapyrazoles, benzothiopyranoindoles, 3,4-benzpyrene, benzopyrene diol epoxidie, 1-pyrenyloxirane, benzanthracene-5,6-oxide, benzodipyrones, benzothiazoles, quinolones, chloroquine, quinine, phenylquinoline carboxamides, furocoumarins, such as psoralens and isopsoralens, ethidium salts, propidium, coralyne, ellipticine cation and derivatives, polycyclic hydrocarbons and their oxirane derivatives, and echinimycin; b) minor groove binders such as distamycin, mitomycin, netropsin, other lexitropsins, Hoechst 33258 and other Hoechst dyes, DAPI (4',6'-diamidine-2-phenylindole), berenil, and triarylmethane dyes; c) major groove binders such as aflatoxis; d) molecules that bind by electrostatics (phosphate backbone binders), such as spermine, spermidine, and other polyamines; e) nucleic acids or analogues which bind by such sequence specific interactions as triple helix formation, D-loop formation, and direct base pairing to single stranded targets.

While not limited to any particular mechanism, it is believed that the nucleic acid binding ligand functions as a carrier (or anchor) that targets (or directs) the molecule to nucleic acid, interacting non-covalently therewith.

1. Psoralens as Noncovalent Nucleic Acid Binding Groups

The present invention contemplates a specific class of compounds which use a psoralen group as a nucleic acid binding group. These compounds are particularly suitable for use in the present invention. Previous nucleic acid specific alkylating agents typically contain an alkylating moiety such as a chloroethylamine fragment, connected to a nucleic acid specific group, an intercalator (e.g., acridine), or a minor groove binder. These moieties are mutagenic in themselves. After the residual alkyating agent has been hydrolysed from the compound, the residue may still be rather mutagenic. In contrast, compounds having a psoralen nucleic acid binding group display substantially reduced mutagenicity, thus providing an improved safety factor. Psoralens are well known as nucleic acid intercalators but their utility has mainly been as photoactive agents which covalently bind to the nucleic acids upon irradiation with UVA (320–400 nm). Without intending to be bound to any mechanism of action of the present invention, it is hypothesized that the role of the psoralen group in the compounds described here is as an intercalator to increase the specificity of location of the alkylating agent, and thus the specificity of the alkylation reaction to nucleic acids.

Specifically some novel compounds of the present invention contain psoralens [7H-furo(3,2-g)-(1)-benzopyran-7-one, or b-lactone of 6-hydroxy-5-benzofuranacrylic acid], which are linear molecules:

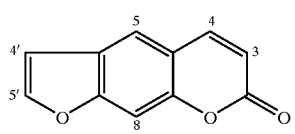

and in which the two oxygen residues appended to the central aromatic moiety have a 1, 3 orientation, and further in which the furan ring moiety is linked to the 6 position of the two ring coumarin system. Psoralen derivatives are derived from substitution of the linear furocoumarin at the 3, 4, 5, 8, 4', or 5' positions.

A psoralen of the present invention is represented in the structure below, wherein one or two of $R_1$, $R_2$, $R_3$, $R_4$, or $R_5$ are a (2-chloroethyl)amino group, optionally with a second 2-chloroethyl group on the amine, attached to a psoralen by a chain of one to nine carbons. The chain can contain one or more heteroatoms of the group comprising oxygen, nitrogen or sulfur. The chain can optionally contain one or more unsaturated bonds or carbonyl groups. The chain is optionally substituted with lower alkyl groups.

Specifically the novel compounds contain a psoralen where one or two of R1, R2, R3, R4, or R5 are a (2-chloroethyl)amino group or (2-bromoethyl)amino group, optionally with a second 2-haloethyl group on the amine, attached to a psoralen by a chain of one to nine carbons. The chain can contain one or more heteroatoms of the group comprising oxygen, nitrogen or sulfur. The chain can optionally contain one or more unsaturated bonds or carbonyl groups. The chain is optionally substituted with lower alkyl groups.

Positions R1–R5 unoccupied by the alkylating group may be hydrogen, lower alkyl, lower alkoxy, halogen, CH2OR6 or CH2NR7R8 (where R6–R8 are hydrogen or lower alkyl).

The compounds may be neutral amines, or their salts.

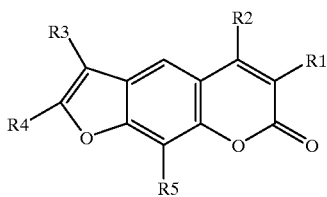

Ring construction of psoralens, and their functionalization with displaceable groups, X, (where X=Cl, Br, I, $OSO_2CH_3$, etc,) is described in the literature (Hearst et al, U.S. Pat. Nos. 4,124,598; 4,196,281; Kaufman, U.S. Pat. Nos. 4,269,851; 4,269,852; 4,294,822; 4,298,614; 4,370,344; Wollowitz et al., U.S. Pat. No. 5,399,719; Antonello, S. C., et al., *Farmaco* (1978) 34, 139).

The desired products are constructed by one of three routes. In the first, a 2-hydroxyethylamine (e.g., diethanolamine) is reacted directly with psoralen-$(CH_2)_nX$ where X is a readily displaceable group such as a halide, mesylate or tosylate. The chain is attached to the psoralen at the 3,4,4',5', or 8 positions, other substituents may be on the psoralen ring, and n=1–6. In a second steps, the hydroxy groups of the intermediate are then converted to chloro or bromo groups by standard means, for example with thionyl chloride to give the desired product.

In the second route, the functionalized psoralen is reacted with HY—$(CH_2)_m$—OH, where Y=NH, S, O and m=2–6). The terminal alcohol is then converted to a readily displaceable group (halo, mesylate, etc.) by standard means, then reacted with the (2-hydroxyethyl)amine. The resultant compound is converted into a haloethylamine-functionalized product as described above.

In the final route, the HY—$(CH_2)_m$—$N(CH_2CH_2OH)_2$, where m=2 to 6, is prepared as described in the literature (e.g., Peck, R. M., Preston, R. K., Creech, H. J., *J. Amer. Chem. Soc.*, (1959) 81, 3984), and reacted directly with the functionalized psoralen. Again, conversion of the hydroxy groups to halides gives the desired psoralen mustard products.

B. Mustard Group

The second characteristic that compounds of the present invention have in common is that they contain at least one mustard group. A "mustard group" is defined here as including mono or bis haloethylamine groups, and mono haloethylsulfide groups.

The present invention is not limited strictly to mustards. It is believed that mustards can form reactive intermediates such as aziridinium or aziridine complexes and sulfur analogs of these complexes. The present invention also contemplates functional groups that are the equivalent of mustards, such as epoxides.

While not limited to any particular mechanism, compounds having mustard groups are known to react with nucleic acids to form covalent complexes which inhibit nucleic acid replication. They are typically solids that, upon dissolution in a medium which contains nucleophiles, completely react within minutes or hours. Some examples are shown below.

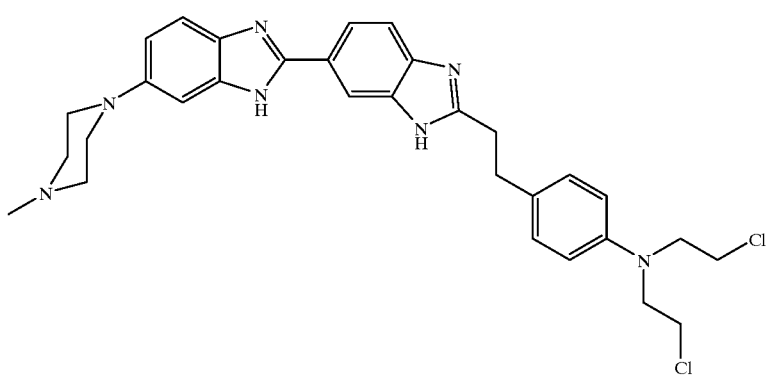

Hoechst mustard (CRL)

-continued

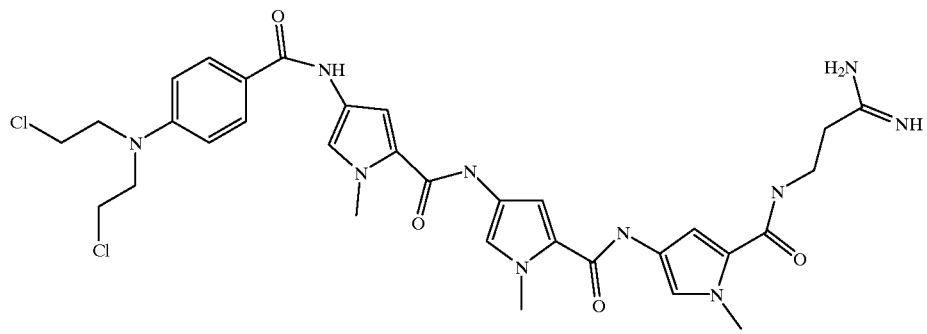

FCE 24517 (Farmitalia)

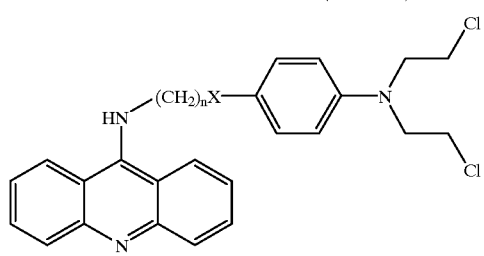

X = CH$_2$, NH, O, S

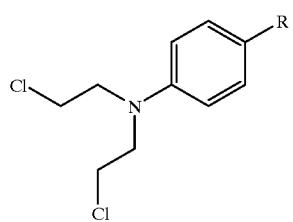

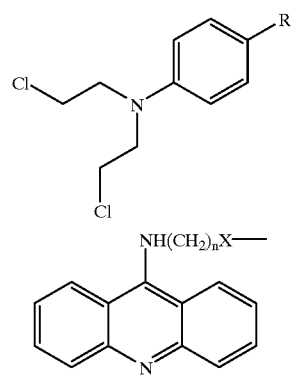

Nitrogen mustards thoroughly described in the literature. E.g., see Gravatt, G. L., et al., "DNA-Directed Alkylating Agents. 4. 4-Anilinoquinoline-Based Minor Groove Directed Aniline Mustards," *J. Med. Chem.* 34:1552 (1991); Cummings, J., et al., "Determination of Reactive Nitrogen Mustard Anticancer Drugs in Plasma by High-Performance Liquid Chromatography Using Derivatization," *Anal. Chem.* 63:1514 (1991). They are known to be potent alkylators of nucleic acid and due to this mode of action, they have been widely studied as antitumor agents. Several have found practical use in the clinic (e.g. aniline mustard, chlorambucil, melphalan).

One class of nitrogen mustards is the aniline mustards. These compounds have at least one haloethylaminoaniline group on it, where the haloethyl may be mono or bis. An example of a bis(haloethyl)aminoaniline group appears below (where R is the point of linkage to other groups):

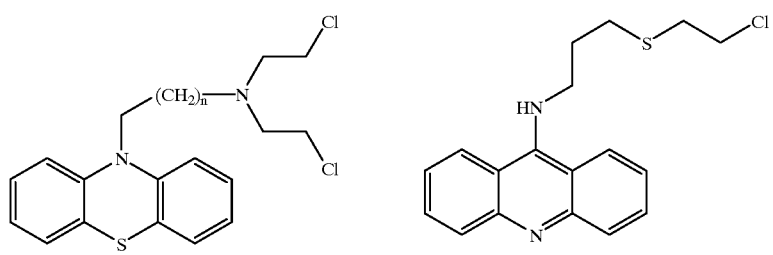

A specific aniline mustard group is the acridine carried aniline mustards (described in Gravatt, et al., J. Med. Chem. 34:1552), where R comprises a linking group (for example O, CH$_2$, S, COHN, or CO, however, other linking groups are contemplated) which links the mustard group to a second component, an acridine group. An example of the components of a 9-aminoacridine carried aniline mustard appears below (where X is the linking group):

The present invention demonstrates that a specific compound having a nucleic acid binding ligand and a mustard group, N1,N1-bis (2-chloroethyl)-N4-(6-chloro-2-methoxy-9-acridinyl)-1,4-pentanediamine dihydrochloride ("quinacrine mustard"), is useful as an antiviral agent for red cells. Quinacrine mustard is commercially available (from Aldrich, Milwaukee, Wis., as quinacrine mustard dihydrochloride hydrate, structure shown below).

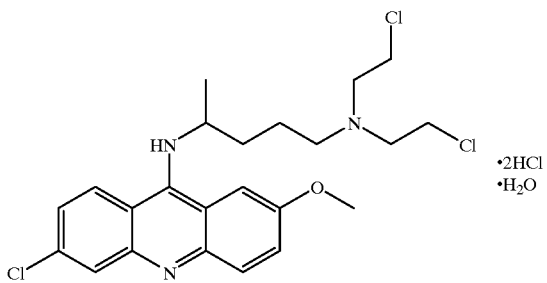

II. MATERIALS FOR DECONTAMINATION

The present invention contemplates novel compounds and a new use for compounds having a nucleic acid binding ligand and a mustard group: the inactivation of viruses and bacteria in blood, blood products and other biological compositions. While not an exclusive list, the following biological compositions are contemplated, and are referred to generally as "samples". Of the blood and blood components contemplated, exemplary compositions include whole blood, packed red cells, platelets, plasma (fresh or fresh frozen plasma), and proteins derived from blood or blood components. Blood components also encompass plasma protein portion, antihemophilic factor (AHF, Factor VIII); Factor IX and Factor IX complex (Factors II, VII, IX and X); fibrinogens, Factor XIII, prothrombin and thrombin (Factor II and IIa); immunoglobulins (e.g. IgA, IgD, IgE, IgG and IgM and fragments thereof e.g. Fab, $F(ab')_2$, and Fc); hyper-immune globulins as used against tetanus and hepatitis B; cryoprecipitate; albumin; interferons; lymphokines; and transfer factors. The present invention also contemplates, as part of blood and blood products, a synthetic version of any blood or blood product.

Other biological compositions which are contemplated by the present invention include vaccines, recombinant DNA produced proteins, oligopeptide ligands, etc. Biological compositions also encompass clinical samples other than blood and blood components, such as urine, sputum, feces, spinal fluid, and other materials removed from mammals for clinical testing.

III. INACTIVATION OF PATHOGENS

The present invention contemplates treating a blood product with a compound having a nucleic acid binding ligand and a mustard group to inactivate contaminating pathogen nucleic acid sequences before using the blood product.

A. Inactivation In General

The term "inactivation" is here defined as the altering of the nucleic acid of a unit of pathogen so as to render the unit of pathogen incapable of replication. This is distinct from "total inactivation", where all pathogen units present in a given sample are rendered incapable of replication, or "substantial inactivation," where most of the pathogen units present are rendered incapable of replication. "Inactivation efficiency" of a compound is defined as the level of inactivation the compound can achieve at a given concentration of compound or dose of irradiation. For example, if 100 μM of a hypothetical compound X inactivated 5 logs of HIV virus whereas under the same experimental conditions, the same concentration of compound Y inactivated only 1 log of virus, then compound X would have a better "inactivation efficiency" than compound Y.

To appreciate that an "inactivation" method may or may not achieve "total inactivation," it is useful to consider a specific example. A bacterial culture is said to be inactivated if an aliquot of the culture, when transferred to a fresh culture plate and permitted to grow, is undetectable after a certain time period. A minimal number of viable bacteria must be applied to the plate for a signal to be detectable. With the optimum detection method, this minimal number is 1 bacterial cell. With a sub optimal detection method, the minimal number of bacterial cells applied so that a signal is observed may be much greater than 1. The detection method determines a "threshold" below which the "inactivation method" appears to be completely effective (and above which "inactivation" is, in fact, only partially effective).

B. Inactivation of Potential Pathogens

The same considerations of detection method and threshold exist when determining the sensitivity limit of an inactivation method for nucleic acid. Again, "inactivation" means that a unit of pathogen is rendered incapable of replication.

In the case of inactivation methods for material to be used by humans, whether in vivo or in vitro, the detection method can theoretically be taken to be the measurement of the level of infection with a disease as a result of exposure to the material. The threshold below which the inactivation method is complete is then taken to be the level of inactivation which is sufficient to prevent disease from occurring due to contact with the material. It is recognized that in this practical scenario, it is not essential that the methods of the present invention result in "total inactivation". That is to say, "substantial inactivation" will be adequate as long as the viable portion is insufficient to cause disease. Thus "substantially all" of a pathogen is inactivated when any viable portion of the pathogen which remains is insufficient to cause disease. The inactivation method of the present invention renders nucleic acid in pathogens substantially inactivated. In one embodiment, the inactivation method renders pathogen nucleic acid in blood preparations substantially inactivated.

Without intending to be limited to any method by which the compounds of the present invention inactivate pathogens, it is believed that inactivation results from alkylation of portions of the pathogen nucleic acid. Further, while it is not intended that the inactivation method of the present invention be limited by the nature of the nucleic acid; it is contemplated that the inactivation method render all forms of nucleic acid (whether DNA, mRNA, etc.) substantially inactivated.

When a compound having a nucleic acid binding ligand and a mustard group is used to modify nucleic acid, the interaction of the pathogen nucleic acid (whether DNA, mRNA, etc.) with the compound preferably prevents replication of the pathogen, such that, if a human is exposed to the treated pathogen, infection will not result.

"Synthetic media" is herein defined as an aqueous synthetic blood or blood product storage media. In one embodiment, the present invention contemplates inactivating blood products in synthetic media comprising a buffered saline solution.

The present method inactivates nucleic acid based pathogens present in blood through a single procedure. Thus, it has the potential to eliminate bacteria, protozoa, and viruses as well. It is not intended that the present invention be limited by the number or nature of pathogens inactivated. Importantly, however, the treatment of the present invention has been found to block the replication of the HIV virus. Had an effective decontamination method been available prior to the advent of the AIDS pandemic, no transfusion associated HIV transmission would have occurred. Decontamination based on compounds having a nucleic acid binding ligand and a mustard group has the potential to eliminate all infectious agents from the blood supply, regardless of the pathogen involved.

C. Selecting Compounds for Inactivation of Pathogens

In order to evaluate a compound to decide if it would be useful in the decontamination methods of the present invention, two important properties should be considered: 1) the compound's ability to inactivate pathogens and 2) its mutagenicity after treatment. The ability of a compound to inactivate pathogens may be determined by several methods. One technique is to perform a bacteriophage screen; an assay which determines nucleic acid binding of test compounds. A screen of this type, an R17 screen, is described in detail in an example, below. If the R17 screen shows inactivation activity, it is useful to directly test the compound's ability to inactivate a virus. One method of performing a direct viral inactivation screen is described in detail in an example below for cell free HIV.

The R17 bacteriophage screen is believed to be predictive of HIV inactivation efficiency, as well as the efficiency of compounds against many other viruses. R17 was chosen because it was expected to be a very difficult pathogen to inactivate. It is a small, single stranded RNA phage. Without intending to be limited to any means by which the present invention operates, it is expected that shorter pieces of nucleic acid are harder to inactivate because they provide a smaller target for the compound. Thus it is expected that under conditions that result in the inactivation of R17 the inactivation of many viruses and bacteria will also be obtained.

The cell free HIV screen complements the R17 screen by affirming that a given compound which has tested positive in R17 will actually work effectively to inactivate viruses. Thus, if a compound shows activity in the R17 screen, it is next tested in the viral inactivation screen.

The second property that is important in testing a compound for use in methods of the present invention is mutagenicity after treatment. The most widely used mutagen/carcinogen screening assay is the Ames test. This assay is described by D. M. Maron and B. N. Ames in Mutation Research, 113: 173 (1983) and a specific screen is described in detail in an example, below. The Ames test utilizes several unique strains of *Salmonella typhimurium* that are histidine-dependent for growth and that lack the usual DNA repair enzymes. The frequency of normal mutations that render the bacteria independent of histidine (i.e., the frequency of spontaneous revertants) is low. The test allows one to evaluate the impact of any residual chemical entities that remain after treatment on this revertant frequency.

Because some substances are not mutagenic by themselves, but are converted to a mutagen by metabolic action, the compound to be tested is mixed with the bacteria on agar plates along with the liver extract. The liver extract serves to mimic metabolic action in an animal. Control plates have only the bacteria and the extract.

The mixtures are allowed to incubate. Growth of bacteria (if any) is checked by counting colonies. A positive Ames test is one where the number of colonies on the plates with mixtures containing the compound significantly exceeds the number on the corresponding control plates.

When known carcinogens are screened in this manner with the Ames test, approximately ninety percent are positive. When known noncarcinogens are similarly tested, approximately ninety percent are negative.

A compound (X) can be evaluated as a potential decontamination compound for use in the present invention, as shown in Table 1, below. X is initially evaluated in Step I. X is screened in the R17 assay, in the presence of red blood cells, at several different concentrations between 4 and 320 $\mu$M, as explained in an example below. If the compound shows inactivation activity greater than 1 log inactivation of R17 (log kill) in the R17 screen at any concentration, the compound is then screened in the cell free HIV assay, Step II, as explained in an example below. If the compound shows inactivation activity greater than 1 log inactivation of HIV (log kill) in the cell free HIV assay, the compound is a useful agent for inactivation of pathogens in clinical test samples. If the compound is being evaluated for decontamination of biological materials to be used in vivo, it is then taken through Step III. A biological material decontaminated by a method of the present invention is screened in the Ames assay to determine whether any compound that remains after decontamination is mutagenic. Finally, if the residual material does not show significant mutagenicity in the Ames assay, the compound is identified as a useful agent for inactivation of pathogens in products to be used in vivo as well.

TABLE 1

| STEP | SCREEN | RESULT | INTERPRETATION |
| --- | --- | --- | --- |
| I | R17 | >1 log kill by any concentration | potential compound, go to step 2 |
| | | <1 log kill | compound is ineffective as an inactivation treatment |
| II | Viral Inactivation | >1 log kill by any concentration | useful for clinical sample decontamination go to step 3 |
| | | <1 log kill | compound is ineffective as an inactivation treatment |
| III | Ames | less mutagenic than AMT | useful agent for inactivation |

By following these instructions, a person can determine which compounds would be appropriate for use in methods of the present invention.

D. Delivery and Removal of Compounds for Inactivation

The present invention contemplates several different formulations and routes by which the compounds described herein can be delivered in an inactivation method, and where desired, removed. This section is merely illustrative, and not intended to limit the invention to any form or method of treatment with the compounds.

The compounds of the present invention may be introduced in an inactivation method in several forms and at various times, which may depend on the purpose for which the blood preparation is decontaminated. The compounds may, for example, be introduced as an aqueous solution in water, saline, a synthetic media or a variety of other media. The compounds may alternatively be provided as dry formulations, with or without adjuvants. Further, the compounds may be introduced alone, or in a "cocktail" or mixture of several different compounds. In a preferred embodiment, a compound having a nucleic acid binding ligand and a mustard group is employed at a concentration less than 250 $\mu$M.

The compounds can be mixed directly with the blood or blood product or prepared as a solution or suspension in a bio-compatible fluid [such as Adsol (the contents of which are set forth in the Experimental section, below) or an organic solvent (e.g. dimethyl sulfoxide (DMSO), ethanol, glycerin, polyethylene glycol (PEG) or polypropylene glycol)] and then mixed with the blood. The new compounds may also be provided at different points in the inactivation process. For example, the compound may be introduced to the reaction vessel, such as a blood bag, at the point of manufacture. Alternatively, the compound may be added to the material to be sterilized after the material has been placed in the reaction vessel.

1. Decontamination of Clinical Samples.

A clinical sample is defined as any material removed from mammals for clinical testing, including, but not limited to blood and blood components, urine, sputum, feces, bone marrow, and spinal fluid. A serum analyte is defined here as a component found in clinical samples which is measured in clinical chemistry tests. Examples of serum analytes include, but are not limited to: glucose, blood urea nitrogen, creatinine, blood urea nitrogen/creatinine ratio, sodium, potassium, chloride, magnesium, calcium, phosphorous inorganic, total protein, albumin, total globulin, albumin/globulin ratio, billirubin, alkaline phosphatase, lactate dehydrogenase, glutamate transferase, aspartate transaminase, alanine aminotransferase, uric acid, iron, triglycerides, and cholesterol.

In the decontamination of clinical samples, the goal is to decontaminate the sample so that infectious agents cannot be transferred to clinical laboratory workers. Because the samples will not be transfused into a recipient, there is less concern that residual compound be removed from the sample. Thus scrubbing techniques may not be desired. The present invention contemplates that the compound may be in the clinical sample test tube prior to drawing the sample from the patient, or it may be added after drawing. Once the compound has contacted the sample, the sample preferably is thoroughly mixed, then incubated. The sample may then be screened in the desired panel of clinical chemistry tests without concern for spreading infectious diseases.

2. Decontamination of Blood Products for Transfusion.

The compound for decontamination may be introduced to the whole blood prior to fractionating, by adding to the blood bag before or after blood is drawn. Alternatively, the compound may be added after fractionation of the blood, decontaminating the individual fractions.

In products for transfusion, in some cases it may be desirable to remove residual compound or chemical products of the reaction after treatment of the product but prior to transfusion. The present invention contemplates the removal, or "scrub" of the compound from the blood product post illumination and prior to transfusion. In one embodiment, any residual compound or chemical product may be removed using an adsorbent material. Examples of adsorbent materials which may be used in the present invention include, but are not limited to: activated charcoal (either uncoated or coated with a polymer), silica, reverse phase silica, polymeric adsorbents, and modified polymeric adsorbents. The present invention contemplates several ways for the introduction of the adsorbent material to the blood products for transfusion. The adsorbent may be mixed directly with the blood products and subsequently filtered out. Alternatively, the blood products could be passed through a filter containing the adsorbent material.

3. Decontamination of Vaccines and Other Biological Compositions

Vaccines and other biological compositions which are not derived from blood, such as recombinant DNA produced proteins and oligopeptide ligands, may also be decontaminated using methods of the present invention. Recombinant DNA produced proteins often are manufactured in large quantities in host organisms. Introduction of the decontamination compound may occur prior to amplification, so that as the host organisms grow, the compound is incorporated into the organism. Alternatively, the compound may be added after manufacture, but before the product is introduced into a mammal.

Removal of the compound before use may be desired here as well as with blood products for transfusion. Those methods mentioned above apply equally well in the case of vaccines and other biological compositions.

V. PRESERVATION OF BIOCHEMICAL PROPERTIES OF TREATED MATERIAL

When treating blood products to be used in vivo, one must ask whether the process or the compounds used alter the in vivo activity of the treated material. For example, red blood cell transfusion is a well established efficacious treatment for patients suffering large blood loss. However, if the inactivation treatment used greatly reduces the in vivo life of the red blood cells, then the treatment has no practical value. The compounds of the present invention are useful in inactivation procedures because the reaction can be carried out at temperatures compatible with retaining biochemical properties of blood and blood products. But not all methods of pathogen inactivation will inactivate without significantly lowering the biological activity of the decontaminated material. Previously known compounds and protocols for inactivation have necessitated both exposure to light and the subsequent removal of molecular oxygen from the reaction before and during the exposure, to prevent damage to blood products from oxygen radicals produced during irradiation. See L. Lin et al., Blood 74:517 (1989); U.S. Pat. No. 4,727,027, to Wiesehahn. The present invention may be used to decontaminate blood products without light, and in the presence of oxygen, without destroying the activity for which the products are prepared. Further, with methods of the present invention, there is no need to reduce the concentration of molecular oxygen.

The present invention contemplates that in vivo activity of a blood product is not destroyed or significantly lowered if the blood product which is decontaminated by methods of the present invention tests as would a normally functioning blood product in known assays for function of the particular blood product. The activity of a clinical sample is not destroyed or significantly lowered if the clinical sample which is decontaminated by methods of the present invention tests as would an untreated sample in common clinical chemistry tests. In contrast, a blood product or clinical sample is considered to have incurred "significant damage" when the blood product no longer functions for the purpose it was prepared. For example, where red blood cells are concerned, in vivo activity is not destroyed or significantly lowered if AMP levels, IgG binding, and extracellular potassium levels of the red blood cells are substantially the same in red blood cells treated by the methods of the present invention and stored 9 days as they are in untreated samples stored for 9 days. Similarly, a clinical sample has not suffered significant damage if a treated sample tests substantially the same as an untreated sample in one or more common clinical chemistry tests. "Substantially the same" means that the values of the treated samples do not exhibit change which is more than 10% larger than change in values exhibited in a non treated control. In the case of red blood cells, this comparison is made after a 9 day storage following treatment.

VI. PREPARATION OF VACCINES

The preparation of viral vaccines is also contemplated by methods of the present invention. The present invention contemplates producing vaccines to a wide variety of viruses, including human viruses and animal viruses, such as canine, feline, bovine, porcine, equine and ovine viruses.

The contemplated method is suitable for inactivating double stranded DNA viruses, single stranded DNA viruses, double-stranded RNA viruses and single-stranded RNA viruses, including both enveloped and non-enveloped viruses. A contemplated method for producing a vaccine for inoculation of a mammalian host susceptible to infection by a virus comprises growing culture of virus, isolated from an infected host, in a suitable mammalian cell culture, exposing at least one of the seed viruses to a compound having a nucleic acid binding ligand and a mustard group for a time sufficient to inactivate the virus to a non-infectious degree, under conditions which substantially preserve the antigenic characteristics of the inactivated viral particles, and combining said inactivated virus with a suitable adjuvant.

The inactivated virus may be formulated in a variety of ways for use as a vaccine. The concentration of the virus will generally be from about $10^6$ to $10^9$ plaque forming units (pfu)/ml, as determined prior to inactivation, with a total dosage of at least $10^5$ plaque forming units per dose (pfu/dose), usually at least $10^6$ pfu/dose, preferably at least $10^7$ pfu/dose. The total dosage will usually be at or near about $10^9$ pfu/dose, more usually being about $10^8$ pfu/dose. The vaccine may include cells or may be cell-free. It may be an inert physiologically acceptable medium, such as ionized water, phosphate-buffered saline, saline, or the like, or may be administered in combination with a physiologically acceptable immunologic adjuvant, including but not limited to mineral oils, vegetable oils, mineral salts, and immunopotentiators, such as muramyl dipeptide. The vaccine may be administered subcutaneously, intramuscularly, intraperitoneally, orally, or nasally. Usually, a specific dosage at a specific site will range from about 0.1 ml to 4 ml, where the total dosage will range from about 0.5 ml to 8 ml. The number of injections and their temporal spacing may be highly variable, but usually 1 to 3 injections at 1, 2 or 3 week intervals are effective.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); N (Normal); mol (moles); mmol (millimoles); $\mu$mol (micromoles); nmol (nanomoles); gm (grams); mg (milligrams); $\mu$g (micrograms); L (liters); ml (milliliters); $\mu$l (microliters); cm (centimeters); mm (millimeters); $\mu$m (micrometers); nm (nanometers); °C. (degrees Centigrade); HPLC (High Pressure Liquid Chromatography); Q (quinacrine); QM (quinacrine mustard); DMSO (dimethylsulfoxide); Htc (hematocrit); RBC (red blood cell); LB (Luria Broth); N-acetyl-cysteine (NAC); BUN (blood urea nitrogen); Creat. (creatinine); phos acid (phosphoric acid); alk (alkaline phosphatase); ALT (Alanine Aminotransferase); AST (Aspartate Transaminase); LDH (lactate dehydrogenase); GGT (Glutamate Transferase); cfu (culture forming units); pfu (plaque forming units); DMEM (Delbecco's modified eagles medium); FBS (fetal bovine serum); PRBC (packed red blood cells); PCR (polymerase chain reaction); rpm (revolutions per minute); TC (tissue culture); NHSP (normal human serum pool); LSM (lymphocyte separation medium); NCS (newborn Calf Serum); PBS (phosphate buffered saline).

While it is available commercially from Baxter Heathcare Corp, Deerfield, Ill., Adsol used in the following experiments was made by sterile filtering the following mixture: 22 g glucose, 9 g NaCl, 7.5 g mannitol, and 0.27 g adenine in 1 liter of distilled H2O.

The polymerase chain reaction (PCR) is used in some of the examples below. PCR is a method for increasing the concentration of a segment of a target sequence in a mixture of genomic DNA without cloning or purification. See K. B. Mullis et al., U.S. Pat. Nos. 4,683,195 and 4,683,202, hereby incorporated by reference. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then are annealed to their complementary sequences within the target molecule. Following annealing, the primers are extended with a polymerase so as to form a new pair of complementary strands. The steps of denaturation, primer annealing, and polymerase extension can be repeated many times (i.e. denaturation, annealing and extension constitute one "cycle;" there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to by the inventors as the "polymerase chain reaction".

EXAMPLE 1

This example measures the R17 inactivation activity of quinacrine mustard (QM) solutions made in either Adsol or DMSO. The bacteriophage R17 has a single stranded RNA genome of approximately $1.2 \times 10^6$ daltons, and is difficult to inactivate compared to many other targets. See generally L. Lin et al., Blood 74:517 (1989). The advantage of the R17 system is that inactivation can be readily assayed in the laboratory.

The assay used to determine inactivation measures the ability of the phage to subsequently infect bacteria and inhibit their growth. The phage was grown up in Hrf 3000 bacteria. (R17 and Hrf 3000 were obtained from American Tissue Culture Collection (ATCC), Washington, D.C.). First, the R17 stock virus was diluted (10.9 logs/ml in LB broth) 1:20 in Adsol (R17-Adsol). Then a 30% hematocrit (Htc) red blood cell concentrate in R17-Adsol mixture was prepared by spinning down red blood cells (RBC) from whole blood and resuspending 3.5 ml RBC pellet in 7.0 ml R17-Adsol. In this, and the following experiments, Htc was measured on a Model F800 Sysmex cell counter (Toa Medical Electronics, Kobe, Japan). Ten 1 ml aliquots of the samples were then transferred to sterile tubes.

Approximately 2 mg of QM, commercially available from Aldrich, Inc., Milwaukee, Wis., was weighed out into each of two tubes. Samples were then dissolved in DMSO or Adsol, respectively, to a final concentration of 0.4 mg/ml. QM in Adsol is a suspension, not a solution, at this concentration.

Next, the QM suspension was added to the R17-Adsol samples to achieve the following final concentrations of QM in the sample tubes: 2.5, 5.0, 10, or 20 $\mu$g/ml. The QM was completely solubilized at these concentrations. Positive control samples were also prepared, where 50 $\mu$l of either Adsol or DMSO was added to R17-Adsol samples. The samples were allowed to stand at room temperature for at least 1 hour. Then the samples were titered by an R17 phage assay. Sterile 13 ml dilution tubes were prepared with LB broth. To make the dilutions, a 0.1 ml aliquot of the solution of phage was added to the first dilution tube of 0.4 ml of media. Then 0.02 ml of this solution was added to the second tube of 0.5 ml media (1:25). The second solution was the diluted serially (1:25) into the remaining tubes. To each diluted sample was added 0.05 ml of Hrf 3000 bacteria cultured overnight and 3 ml of molten LB top agar. The mixed materials were poured onto LB broth plates. After the top agar hardened, the plates were incubated at 37° C. overnight. Plaques were counted the following morning and the titer of the phage remaining after treatment was calculated based on the dilution factors.

The results are shown in Table 2, below, and FIG. 1. It is clear from the data that even at concentrations as low at 2.5 μg/ml QM is effective in inactivating R17. At concentrations above 10 μg/ml, complete inactivation is achieved, to the limit of detection of this assay.

TABLE 2

| Sample # | (QM) (μg/ml) | Solvent | Log Titer |
| --- | --- | --- | --- |
| 1 | 0 | Adsol | 9.8 |
| 2 | 0 | DMSO | 9.8 |
| 3 | 2.5 | Adsol | 3.25 |
| 4 | 5 | Adsol | 3.55 |
| 5 | 10 | Adsol | 1.0 |
| 6 | 20 | Adsol | 1.3 |
| 7 | 2.5 | DMSO | 5.2 |
| 8 | 5 | DMSO | 2.3 |
| 9 | 10 | DMSO | 2.4 |
| 10 | 20 | DMSO | 1.0 |

EXAMPLE 2

The purpose of this example is to show that the presence of RBC does not significantly effect R17 inactivation by compounds and methods of the present invention. Two different compounds were tested, QM and Compound 1, the synthesis of which is described in Example 17, below. For QM, the procedure was as follows: first, approximately 60% Htc RBC concentrate was prepared by dilution in Adsol. The sample was again diluted with Adsol into sterile tubes to give RBC concentrate with a final Htc of 2%, 6%, 20% or 60% (0.5 ml final volume in each tube).

Next, an R17 stock (11.3 logs/ml in LB) was diluted 1:10 in Adsol (R17-Adsol). This stock was added (0.5 ml) to each tube to give a final Htc of approximately 1%, 3%, 10% or 30% in 1 ml. A positive control sample was prepared without RBC by combining 0.5 ml of R17-Adsol with 0.5 ml Adsol. QM (3.4 mg) was dissolved in $H_2O$ to reach a final concentration of 0.1 mg/ml. Then a 10 μl aliquot of the QM solution was added to each R17 sample and the samples were incubated approximately 2 hours. A negative control was not treated with QM. The samples were then titered in an R17 phage assay, as described in Example 1, above.

Figure 2:
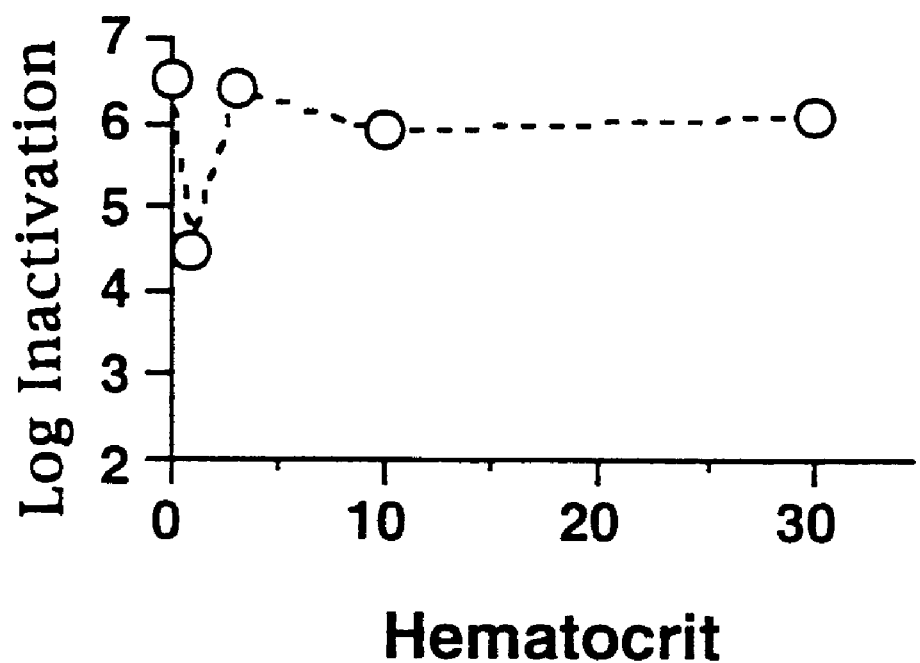
FIG. 2 is a graph showing inactivation of R17 by quinacrine mustard as a function of hematocrit.

The results are shown in Table 3 and FIG. 2. It is clear from the data that QM inactivates R17 in all of the Htc tested.

TABLE 3

| Sample # | Htc (%) | QM (μg/ml) | Log Titer |
| --- | --- | --- | --- |
| 1 | 0 | 0 | 8.8 |
| 9 | 0 | 1.0 | 2.0 |

TABLE 3-continued

| Sample # | Htc (%) | QM (μg/ml) | Log Titer |
| --- | --- | --- | --- |
| 10 | 1 | 1.0 | 4.0 |
| 11 | 3 | 1.0 | 2.1 |
| 12 | 10 | 1.0 | 2.6 |
| 13 | 30 | 1.0 | 2.4 |

Another experiment was performed to test the inactivation ability of a novel compound, Compound 1. A 1:1000 dilution of R17 (stock titer was 11.9 logs) was prepared in 25 ml packed red blood cells. To each of 5 tubes was added 5 ml of this R17-packed red blood cell solution. Compound 1 was then dissolved in saline to a final concentration of 3 mg/ml. The compound in solution was added to the 4 tubes as follows: the first tube, the control tube, received saline only; the second tube received 10 μg/ml of Compound 1 in saline; the third tube received 30 μg/ml of Compound 1 in saline; the forth tube received 100 μg/ml Compound 1 in saline and the final tube received 300 μg/ml of Compound 1 in saline. The tubes were mixed and then incubated at 4° C. overnight. The results showed R17 inactivation activity. Concentrations above 30 μg/ml inactivated approximately 4 logs of R17 with a starting titer of 10 logs of R17.

EXAMPLE 3

This example sets forth the kinetics of R17 inactivation by QM. To measure the kinetics of inactivation, reactive QM must be quenched so that intermediate time points provide a reliable measure of the R17 inactivation at a particular time. Two methods were used here in combination to quench the reaction. First, NAC was added to samples to react with excess QM. Second, samples were rapidly diluted into LB medium to reduce the effective QM concentration in the sample. The control experiments described below demonstrate that this dual approach does effectively quench residual QM, allowing for a valid measure of the reaction kinetics to be taken.

Samples were prepared in the following manner. A dilution of R17 (1:20) into Adsol was prepared: 0.15 ml phage (11.3 logs/ml)+2.85 ml Adsol. An aliquot of sterile-filtered 0.1 M NAC was thawed for use to quench the QM reaction with R17.

Tubes were then prepared for standard dilution of phage, containing appropriate volumes of LB.

TABLE 4

| Sample # | Treatment |
| --- | --- |
| 1 | QM first, NAC quench at 0 min., dilute |
| 2 | QM first, NAC quench at 2 min., dilute |
| 3 | QM first, NAC quench at 4 min, dilute |
| 4 | QM first, NAC quench at 8 min, dilute |
| 5 | QM first, NAC quench at 16 min, dilute |
| 6 | QM first, NAC quench at 32 min, dilute |
| 7 | QM first, NAC quench at 64 min, dilute |
| 8 | QM first, NAC quench at 128 min, dilute |
| 9 | first add NAC, then QM, dilute |
| 10 | first add NAC, then QM, dilute at end |
| 11 | add NAC / no QM, dilute |
| 12 | add NAC / no QM, dilute at end |
| 13 | no NAC / no QM, dilute at end |

A set of tubes were prepared, herein called quenching tubes, containing quenching factors (NAC and/or dilution with LB), to receive the samples at appropriate time points. Cysteine (44 μl aliquots) was added to quenching tubes numbered 1–12.

QM (1.5 mg) was dissolved in Adsol (25.0 ml) to a final concentration of 0.1 mg/ml. Then the QM solution was diluted 100× into Adsol: 50 μl QM solution+4.95 ml Adsol; 1 μg/ml final concentration.

Table 4 sets forth how each control and experimental sample was treated. The controsl were treated first, by placing aliquots (100 μl) of phage into quenching tubes 9–13, then immediately adding 100 μl of 1 μg/ml QM to quenching tubes 9 and 10 and 200 μl Adsol to quenching tubes 11 and 12. Adsol (250 μl) was added to quenching tube 13. Then samples 9 and 11 were diluted into LB broth for phage assay.

The experimental samples were treated next. Phage (1.0 ml) was removed into a sterile 15 ml tube. QM (1.0 ml, 1.0 μg/ml) was added. This mixture was removed (by 200 μl aliquots) into quenching tubes 1–8 at the following times: 0, 2, 4, 8, 16, 32, 64, and 128 minutes. The samples were mixed and immediately diluted into LB broth for phage assay. Finally, samples 10, 12, and 13 were diluted into LB broth for phage assay.

Figure 3:
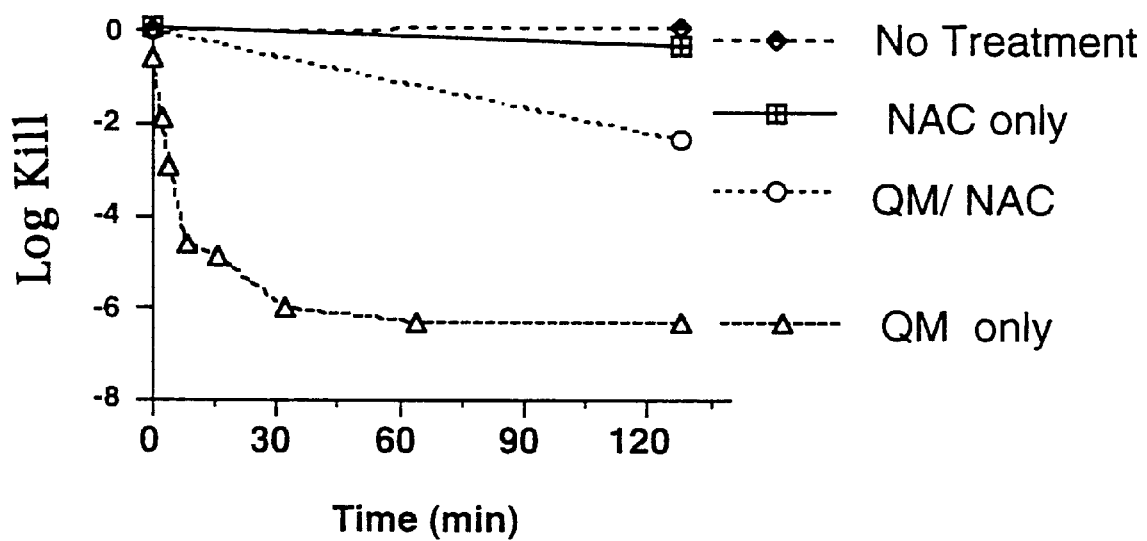
FIG. 3 is a graph showing the inactivation kinetics of quinacrine mustard.

Results are shown in Table 5 and FIG. 3. While NAC alone does not kill R17 (compare samples #11 and #12 with sample #13), when added before QM, NAC provided a substantial, but not complete protection against QM inactivation (compare samples #7 and #10). The combination of NAC and dilution resulted in almost complete quenching of QM activity (compare samples #1 and #13). QM inactivation of R17 was complete within 2 hours.

effects of light in samples that were deliberately exposed to room lights and to examine the inactivation by the parent compound, quinacrine, the structure of which follows:

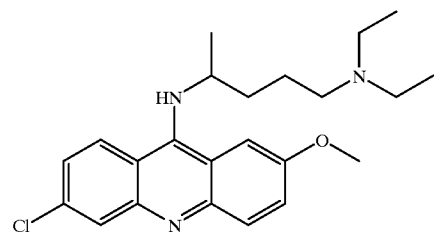

The following procedure was performed in a biosafety cabinet without lights. R17 phage (10.9 logs/ml) was diluted 10 fold into Adsol: 1.0 ml R17 stock+9.0 ml Adsol. One (1) ml of the diluted phage was transferred into ten sterile 1.5 ml tubes. A 0.1 mg/ml QM solution was prepared by dissolving 3.4 mg QM (weighed in hood) with 34 ml $H_2O$. The resulting solution was wrapped in foil to shield from light. Then, 10 μl QM was added to tubes after 0, 10, 40, 60, 120 or 240 minutes of pre-incubation. Samples were again wrapped in foil to prevent exposure to light. For a light control, 10 μl QM was added to 1.0 ml phage at time 0, and

TABLE 5

| Sample | 1 | 2 | 3 | 4 | 5 | 6 | 7 | 8 | 9 | 10 | 11 | 12 | 13 |
|---|---|---|---|---|---|---|---|---|---|---|---|---|---|
| Log Titer | 8.11 | 6.81 | 5.79 | 4.10 | 3.74 | 2.69 | 2.39 | ≦2.4 | 8.66 | 6.32 | 8.73 | 8.35 | 8.80 |

EXAMPLE 4

This experiment measures the loss of QM activity upon pre-incubation of drug in Adsol. It is believed that mustards react by thermally allowed pathways. They can be hydrolyzed in aqueous solution. This experiment was designed to measure loss of QM anti-viral activity in a particular aqueous solution, Adsol. Previous results have shown that QM anti-viral activity did not decrease rapidly upon pre-incubation of the drug in Adsol. (Results not shown). A concern in those experiments was the possibility of light-dependent inactivation, because samples were diluted into LB without making extraordinary efforts to shield ambient light, and because acridines are known to inactivate by photodynamic effects. This experiment was repeated under conditions where ambient light levels were carefully controlled throughout the experiment, in order to exclude the possibility that R17 inactivation was due to light-mediated effects. Also, additional controls were added to examine the the sample was not wrapped in foil. A 1 mg/ml solution of quinacrine in DMSO was prepared as another control. One (1) μl of this was added to each of two samples. Then one sample was incubated in foil (sample Q) and one without foil (sample Q+light). All samples were incubated for 2 hours 15 minutes beyond final addition of QM. Total incubation for the time zero sample was 6 hours 15 minutes.

The following work was performed with very low ambient light (source was one closed doorway): bacteria was diluted and plated in the dark. For the light positive controls, the samples were exposed to ambient light during dilutions, then moved to dim lighting conditions during plating.

Figure 4:
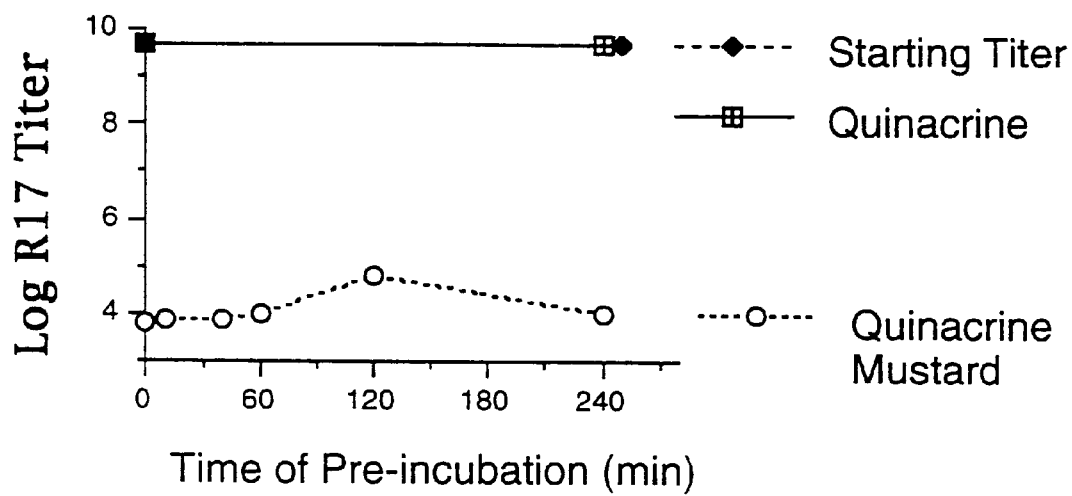
FIG. 4 is a graph showing the reduction in titer of R17 as a function of time of incubation of quinacrine mustard in Adsol.

The results are shown in FIG. 4 and Table 6. From these results it is clear that there was no light-dependent kill by QM or quinacrine under the conditions of this experiment. Further, QM activity was not diminished after a 4 hour pre-incubation in Adsol.

TABLE 6

| Sample | Control | QM + light | Q | Q + light | 0 min | 10 min | 40 min | 1 hour | 2 hour | 4 hour |
|---|---|---|---|---|---|---|---|---|---|---|
| Log Titer | 9.7 | 3.9 | 9.7 | 9.7 | 3.8 | 3.9 | 3.9 | 4.0 | 4.8 | 4.0 |

EXAMPLE 5

QM activity was not diminished after a 4 hour pre-incubation in Adsol, as shown by Example 4, above. A goal of this example is to determine whether QM is inactivated more rapidly by pre-incubation in the presence of red cells. This example also examines the kinetics of removal of QM from red blood cell solutions by an adsorbent material, to establish the effectiveness of a scrub technique in removing compounds containing a mustard group.

First, phage dilutions were prepared. R17 (11.3 log/ml stock) was diluted 1:10 into Adsol: 0.7 ml phage+6.3 ml Adsol. Diluted phage (0.5 ml) was placed into 15 sterile 1.5 ml tubes labeled 1–15. The treatment for each tube is shown in Table 7.

TABLE 7

| Sample # | Treatment | Time (min) |
| --- | --- | --- |
| 1 | none | — |
| 2 | QM-adsol | 0 |
| 3 | QM-adsol | 240 |
| 4 | QM-RBC | 0 |
| 5 | QM-RBC | 15 |
| 6 | QM-RBC | 30 |
| 7 | QM-RBC | 60 |
| 8 | QM-RBC | 120 |
| 9 | QM-RBC | 240 |
| 10 | QM-XAD | 0 |
| 11 | QM-XAD | 15 |
| 12 | QM-XAD | 30 |
| 13 | QM-XAD | 60 |
| 14 | QM-XAD | 120 |
| 15 | QM-XAD | 240 |

Next, QM solutions were prepared. Approximately 20 ml of packed red blood cells (PRBC) were spun down in a 50 ml conical tube at 1600 rpm for 9 minutes. The volume of the pellet after spinning was 17 ml. Approximately 3 mg QM was weighed out on a weighing paper in a biosafety cabinet (actual weight was 4.5 mg). The sample was then transferred to a 50 ml conical tube. The sample was dissolved in Adsol to a concentration of 0.1 mg/ml (actual volume of Adsol was 45 ml). Next, the red blood cell pellet was diluted 1:1 with 17 ml of the QM solution. The tube contents were mixed gently by inversion several times. This is subsequently called the QM-RBC solution.

Amberlite XAD 16™ (a commercially available adsorbent from Sigma, St. Louis, Mo.) was weighed out (0.452 g) and transferred to a 15 ml conical tube. An aliquot of the QM-RBC solution (9 ml) was transferred to the 15 ml tube containing 0.5 g XAD-16 and mixed gently by inversion. This is subsequently referred to as the QM-XAD solution. The QM solution was diluted with an equal volume of Adsol (1 ml of each). This is subsequently referred to as the QM-Adsol solution.

At each time point, 0.1 ml was removed from QM-RBC, QM-XAD and QM-Adsol into a 1.5 ml eppendorf tube. The tubes' contents were spun down 10 sec at full speed in a microfuge to pellet cells and resin. Then 5 μl aqueous phase containing QM was transferred to the appropriate tube containing phage. The phage containing QM was then incubated in the dark for the times specified in Table 7, above. The 240 minute sample was incubated at least 2 hours after addition of QM. Finally, dilutions were made and the phage were plated.

Figure 5:
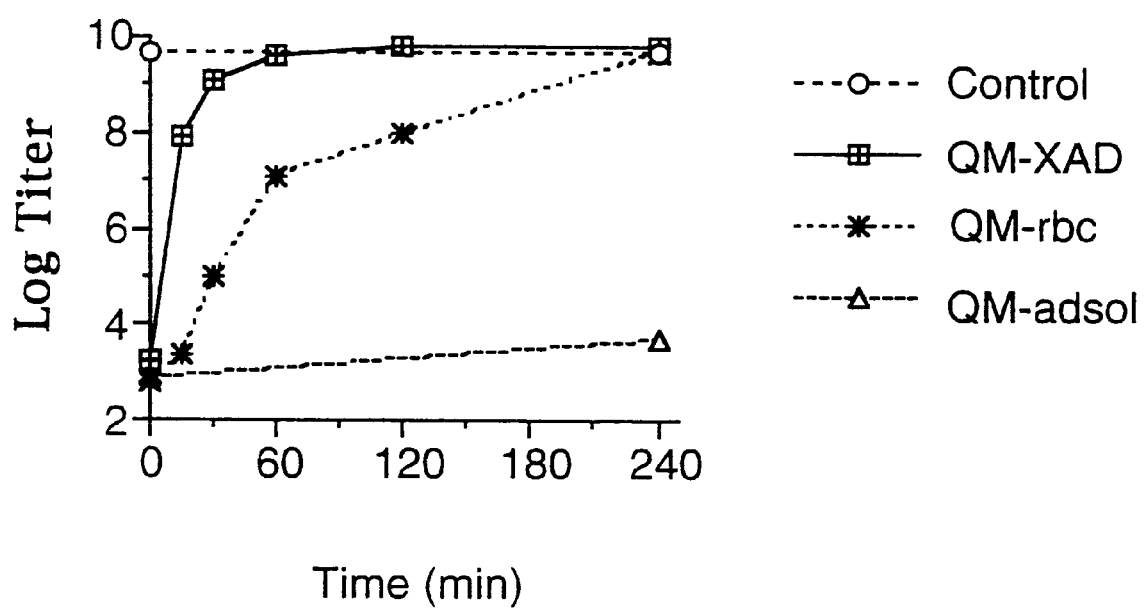
FIG. 5 is a graph showing the reduction in R17 inactivation activity as a function of time when incubated in the presence of either Adsol, red blood cells or Amberlite XAD-16™.

The results appear in Table 8, below, and FIG. 5. QM anti-viral activity was removed upon a 4 hour pre-incubation with red blood cells. The adsorbent scrub material, Amberlite XAD-16™, also removed QM from blood within 1 hour. These results suggest that either incubation in the presence of red blood cells or treatment with an adsorbent resin, or the two treatments combined, will be sufficient to rapidly remove residual QM after inactivation.

TABLE 8

| Sample | Log Titer |
| --- | --- |
| 1 | 9.7 |
| 2 | 2.9 |
| 3 | 3.7 |
| 4 | 2.8 |
| 5 | 3.4 |
| 6 | 5.0 |
| 7 | 7.1 |
| 8 | 8.0 |
| 9 | 9.7 |
| 10 | 3.2 |
| 11 | 7.9 |
| 12 | 9.1 |
| 13 | 9.6 |
| 14 | 9.8 |
| 15 | 9.8 |

EXAMPLE 6

The purpose of this example is to measure inactivation of duck hepatitis B virus (DHBV) by a method of the present invention. DHBV was chosen as a model for human hepatitis B virus because of the similarities in design between the two viruse. See Ganem, D. and Varmus, H. "The Molecular Biology of the Hepatitis B Viruses," Ann. Rev. Biochem. 56:651 (1987).

Infected duck hepatocytes were prepared as follows. Duck hepatocytes were isolated form the livers of appoximately 1 week old ducklings. Ducklings were prescreened and found negative for DHBV. Each of the ducklings was anesthetized, then infused with 0.5 ml sodium heparin via the portal vein. Next, each duckling was perfused with 75 ml of a solution containing 200 ml 1×MEM/Earle's BSS+2 ml Hepes buffer+2 ml of 1% EGTA (in 1×MEM). Then, the ducklings were perfused for 20 minutes with a filter sterilized solution containing 30 mg of Collagenase A (commercially available from Boehringer-Mannheim Biochem., Indianapolis, Ind.)+200 ml Ham's F-12/DMEM medium.

At this point, the liver was removed, cut up into a fine mush and placed in a 125 ml bottle containing 50 ml Ham's F-12/DMEM. Approximately 10 ml of a solution containing 5 mg DNase I and 25 ml Ham's F-12/DMEM was added to the liver suspension. The suspension was spun at 200 rpm for 10 minutes.

The suspension was then strained through gauze pads, the 125 ml bottle was rinsed with the remaining 15 ml of the DNase I solution and the rinsing was also strained into the liver suspension. The cell suspension was equally divided into 2×50 ml centrifuge tubes and pelleted at 50×g for 2 minutes. The pellets were resuspended in 10 ml of a solution containing Medium 199/Earle's BSS, 5% calf serum and pelleted. This process was repeated two more times. The third pelleting was resuspended in 10 ml plating medium. Another 10 ml plating medium was added to each tube.

The liver cell suspension was filtered through a 70 micron cell strainer into a 50 ml centrifuge tube. Aliquots of the cell suspension (approximately 0.5 ml) were transferred to petri dishes containing 2 ml plating medium, to obtain a level of confluency corresponding to approximately 6 to $8 \times 10^6$ viable cells per petri dish. After a two hour incubation at 37°

C., the medium was changed to L-15 medium (commercially available from Gibco, Grand Island, N.Y.) (containing 0.9 g/L galactose, 0.55 g/L Na pyruvate)/DMSO. The medium was again changed at 24 hours and every 48 hours thereafter. Cells were grown in culture for 5–7 days.

Next, viral inactivation was performed. DHBV stock virus was thawed at 37° C. for 15 min in an oven. The virus was then spun down at 14000 rpm in a microfuge for 5 min at room temperature and the supernatant was transferred to a fresh tube, avoiding material at the bottom of the tube. The spin and transfer were repeated and the samples were placed on ice.

Approximately 7 ml of whole blood was drawn into a tube containing acid citrate dextrose anticoagulant. The cells were spun down at 1600 rpm for 9 minutes to pack the red cells. The plasma was withdrawn and replaced with an equal volume of Adsol (2.9 ml).

The virus was diluted 0.25 ml into 2.25 ml red blood cells and the mixture was vortexed to create a $10^{-1}$ dilution. The diluted virus was then aliquoted in sterile tubes as follows: 50 µl as an untreated sample; 1.8 µl to be treated with 40 µg/ml QM; and 0.5 ml to be treated with 10 µg/ml QM. Next, a 1 mg/ml QM solution was prepared by dissolving 3.2 mg QM in 3.2 ml sterile ddH$_2$O. Aliquots of the QM solution were added to the tubes containing virus, as follows: 72 µl QM was added to the 1.8 ml sample to achieve a final concentration of QM of 40 µg/ml and 5 µl QM was added to the 0.5 ml sample to achieve a final concentration of QM of 10 µg/ml. The samples were incubated for 4 hours at room temperature.

After incubation the red blood cells were spun down in a microfuge. Plasma/Adsol supernatant was removed. Dilutions of each sample were prepared by serial dilution of 100 µl virus into 0.9 ml PBS/10% NCS (PBS was 10 mM, pH 7.4). The untreated control (sample #1) was diluted to $10^{-7}$. The treated samples (#2 and #3) was diluted to $10^{-4}$.

Plates containing liver suspension were then inoculated according to the scheme set forth in Table 9. Plates were inoculated with approximately 100 µl virus in duplicate (see below) and cultured for 1, 10, or 15 days. Samples were then analyzed by PCR and by slot blot hybridization to confirm the presence of viral DNA.

Slot blot hybridization was performed for all of the samples after harvesting DNA from tissue culture samples. PCR analysis was performed on selected samples. Samples were denatured with 3M NaOH, as were plasmid pD1.5G DNA samples for labeling. Samples were then neutralized with NH$_4$OAc. 400 µl of 1M NH$_4$OAc was added to each well of a Mini Fold II Slot Blot Apparatus, commercially available from VWR Scientific, Greenbelt, Mo., fitted with a filter, as were aliquots of each sample. Vacuum was applied to the apparatus until all samples had been pulled through the filter. The filter was then baked to dry. Next, the filter was pre-hybridized in a mixture of 250 ml of 20×SSC (175.3 g NaCl, 88.2 g Na citrate in 800 ml H$_2$O), 50 ml of 50×Denhardt's solution (5 g Ficoll, available from Sigma, St. Louis, Mo., 5g polyvinylpyrrolidone, and 5 g bovine serum albumin with 500 ml H$_2$O), 20 ml of h mg/ml denatured salmon sperm DNA, 180 ml H$_2$O, 500 ml formamide and 10 ml of 10% solution of sodium dodecyl sulfate in H$_2$O. Probe was prepared as follows: 3 µl of pD1.5G (67 ng/µl) and 5 ml of 15 ng/µl random hexamer oligonucleotides were heated and cooled again, then 4 µl of 5× labeling buffer, 2 µl of dGAT mixture (5 mM each of dGTP, dATP, dTTP, in TE), 1 µl of Klenow, and 5 µl of [a$^{32}$P]dCTP was added and incubated. Reaction was stopped by adding 25 mM EDTA. Then 5×10$^5$ counts per minute of probe per ml of hybridization solution was added to the filter and allowed to hybridize overnight. The filter was removed, and low stringency wash solution (50 ml of 20×SSC, 940 ml of H$_2$O, and 10 ml of 10% SDS) was added to cover the filter for a wash during shaking, which was repeated 2 times the last time adding high stringency was solution (5 ml of 20×SSC, 990 ml of H$_2$O, and 10 ml of 10% SDS) instead. The filter was then exposed to film to obtain and appropriate exposure, and the film was then scored for positive hybridzation. A negative control sample containing calf thymus DNA was also run.

TABLE 9

| Sample | Treatment | Dilution | Incubation |
|---|---|---|---|
| 1 | no virus | NA | 10 days |
| 2 | untreated | $10^{-7}$ | 10, 15 |
| 3 | untreated | $10^{-6}$ | 10, 15 |
| 4 | untreated | $10^{-5}$ | 10, 15 |
| 5 | untreated | $10^{-4}$ | 10, 15 |
| 6 | untreated | $10^{-3}$ | 10, 15 |
| 7 | 40 µg/ml QM | $10^{-5}$ | 10, 15 |
| 8 | 40 µg/ml QM | $10^{-4}$ | 10, 15 |
| 9 | 40 µg/ml QM | $10^{-3}$ | 10, 15 |
| 10 | 40 µg/ml QM | $10^{-2}$ | 10, 15 |
| 11 | 40 µg/ml QM | $10^{-1}$ | 1, 10, 15 |
| 12 | 10 µg/ml QM | $10^{-5}$ | 10, 15 |
| 13 | 10 µg/ml QM | $10^{-4}$ | 10, 15 |
| 14 | 10 µg/ml QM | $10^{-3}$ | 10, 15 |
| 15 | 10 µg/ml QM | $10^{-2}$ | 1, 10, 15 |

Table 10 summarizes PCR and slot blot hybridization data. (NP signifies that PCR was "not performed" for that sample. A plus sign signifies that DHBV nucleic acid was amplified in PCR. A minus sign signifies that it was not amplified).

TABLE 10

| Sample # | Incubation (days) | Plate #'s | Blot Results | PCR Results |
|---|---|---|---|---|
| 1 | 10 | 1*,2 | -,- | - |
| 2 | 10 | 3,4 | -,- | NP |
| 2 | 15 | 5*,6 | -,- | - |
| 3 | 10 | 7,8 | -,- | NP |
| 3 | 15 | 9*,10 | -,- | + |
| 4 | 10 | 11*,12 | -,- | - |
| 4 | 15 | 13*,14 | ±,+ | + |
| 5 | 10 | 15*,16* | +,- | +,+ |
| 5 | 15 | 17*,18 | +,+ | + |
| 6 | 10 | 19,20* | +,+ | + |
| 6 | 15 | 21*,22 | +,+ | + |
| 7 | 10 | 23,24 | -,- | NP |
| 7 | 15 | 25,26 | -,- | NP |
| 8 | 10 | 27,28 | -,- | NP |
| 8 | 15 | 29,30 | -,- | NP |
| 9 | 10 | 31*,32 | -,- | - |
| 9 | 15 | 33*,34 | -,- | - |
| 10 | 10 | 35*,36 | -,- | - |
| 10 | 15 | 37*,38 | -,- | - |
| 11 | 1 | 39;40* | -,- | - |
| 11 | 10 | 41*,42 | -,- | - |
| 11 | 15 | 43*,44 | -,- | - |
| 12 | 10 | 45,46 | -,- | NP |
| 12 | 15 | 47,48 | -,- | NP |
| 13 | 10 | 49,50* | -,- | - |
| 13 | 15 | 51,52 | -,- | NP |
| 14 | 10 | 53*,54* | -,- | -,- |
| 14 | 15 | 55,56* | -,- | - |
| 15 | 1 | 57*,58 | -,- | - |
| 15 | 10 | 59,60* | -,- | + |
| 15 | 15 | 61*,62 | -,- | + |

*These plates were tested in PCR. Results appear in PCR column.

Referring to Table 10, viral titer was 6 logs per ml based on PCR positive signal for plate #9. A dose of 10 µg/ml QM inactivated 4 logs per ml based on PCR positive signal for plates #60 and #61. A dose of 40 μg/ml QM inactivated >6 logs of DHBV per ml based on the absence of a PCR signal and slot blot signals in all samples tested.

EXAMPLE 7

The purpose of this example is to measure inactivation of cell-free HIV by QM. As in the R17 assay, small aliquots of QM were added to stock HIV-1. The stock QM solution was prepared by dissolving 3.4 mg of the compound in tissue culture media (DMEM/15% FBS) to reach a final concentration of 0.6 mg/ml of QM. The QM was a colloidal suspension rather than a solution at this concentration, which was used in the experiment. Stock HIV ($10^{4.2}$ plaque forming units/ml) was in DMEM/15% FBS. QM solution was added to aliquots of stock HIV-1 to obtain a final total sample volume of 0.5 ml, having the following final concentrations of QM: 3 μg/ml, 10 μg/ml, or 30 μg/ml. The 0.5 ml test aliquots were placed in 24 well polystyrene tissue culture plates. Two controls were prepared, one containing HIV-1 stock only, and one containing QM without HIV-1 stock. All samples were incubated for one hour at room temperature, then stored at −70° C. until assayed for infectivity by a microtiter plaque assay. Aliquots for measurement of residual HIV infectivity in the samples treated with a compound of the present invention were withdrawn and cultured.

Residual HIV infectivity was assayed using an MT-2 infectivity assay. (Previously described in Hanson, C. V., Crawford-Miksza, L. and Sheppard, H. W., J. Clin. Micro 28:2030 (1990)). The assay medium was 85% DMEM (with a high glucose concentration) containing 200 μg of streptomycin, 200 U of penicillin, 50 μg of gentamicin, and 1 μg of amphotericin B per ml, 15% FBS and 2 μg of Polybrene (Sigma Chemical Co., St. Louis, Mo.) per ml. Test and control samples from the inactivation procedure were diluted in 50% assay medium and 50% normal human pooled plasma. The samples were serially diluted in 96-well plates (Corning Glass Works, Corning, N.Y.). The plates were incubated at 37° C. in a 5% $CO_2$ atmosphere for 1 to 18 hours. MT-2 cells (0.025 ml) [clone alpha-4, available (catalog number 237) from the National Institutes of Health AIDS Research and Reference Reagent Program, Rockville, Md.] were added to each well to give a concentration of 80,000 cells per well. After an additional 1 hour of incubation at 37° C. in 5% $CO_2$, 0.075 ml of assay medium containing 1.6% SeaPlaque agarose (FMC Bioproducts, Rockland, Me.), prewarmed to 38.5° C. was added to each well. The plates were kept at 37° C. for a few minutes until several plates had accumulated and then centrifuged in plate carriers at 600×g for 20 minutes. In the centrifuge, cell monolayers formed prior to gelling of the agarose layer. The plates were incubated for 6 days at 37° C. in 5% $CO_2$ and stained by the addition of 0.05 ml of 50 μg/ml propidium iodide (Sigma Chemical Co.) in phosphate-buffered saline (pH 7.4) to each well. After 24 to 48 hours, the pink/orange fluorescence-stained microplaques were visualized by placing the plates on an 8,000 μW/cm² 304 nm UV light box (Fotodyne, Inc., New Berlin, Wis.). The plaques were counted at a magnification of 20× to 25× through a stereomicroscope.

TABLE 11

| Sample | Log Titer |
| --- | --- |
| no QM | 4.2 |
| 3 μg/ml QM | 3.4 |
| 10 μg/ml QM | 2.0 |
| 30 μg/ml QM | <1.7 |

The results appear in Table 11, above. At a concentration of 30 μg/ml, QM was able to inactivate cell-free HIV completely to the level of detection of the plaque assay used.

EXAMPLE 8

The last example demonstrated that QM was able to inactivate cell free HIV. HIV can also be found within certain types of cells. This example examines the ability of QM, at varying concentrations, to inactivate the cell-associated form of HIV.

H9 cells chronically infected with $HIV_{IIIB}$ were used. (H9/HTLV-III-B NIH 1983 Cat.#400). Cultures of these cells were maintained in high glucose Dulbecco Modified Eagle Medium supplemented with 2 mM L-glutamine, 200 units/ml penicillin, 200 μg/ml streptomycin, and 9% fetal bovine serum (Intergen Company, Purchase, N.Y.) For maintenance, the culture was split once a week, to a density of $3 \times 10^5$ to $4 \times 10^5$ cells/ml. About four days after splitting, 8.8% sodium bicarbonate was added as needed. For the inactivation procedure, the cells were used three days after they were split. They were spun from their culture medium at 400 g for 10 minutes, the supernatant was discarded, and the cells were resuspended in approximately 8 ml of 85% DMEM+15% FBS, to a concentration of $2 \times 10^6$ cells/ml. Aliquots (1 ml) of the infected cell suspension were placed in 15 ml tubes for QM free controls and for the QM experimental sample. A stock solution of QM (1 mg/ml in sterile $ddH_2O$) was diluted into the 15 ml tubes in the appropriate aliquots to yield a final concentration of either 0, 3, 10, 30, 100, or 150 μg/ml. The samples were incubated for two hours, with periodic thorough mixing, then stored at −80° C. until analyzed by microtiter plaque assay.

The stored samples were thawed at 37° C., then titrated in an HIV microtiter plaque assay, as described in Hanson, C. V., Crawford-Miksza, L. and Sheppard, H. W., J. Clin. Micro 28:2030 (1990), and as described in Example 7, above, with the following modifications. The samples were serially diluted directly in 96-well plates (Corning Glass Works, Corning, N.Y.). The plates were incubated at 37° C. in a 5% $CO_2$ atmosphere for 1 to 18 hours. MT-2 cells (0.025 mL) [clone alpha-4, available (catalog number 237) from the National Institutes of Health AIDS Research and Reference Reagent Program, Rockville, Md.] were added to each well to give a concentration of 80,000 cells per well. After an additional 1 hour of incubation at 37° C. in 5% $CO_2$, 0.075 mL of assay medium containing 1.6% SeaPlaque agarose (FMC Bioproducts, Rockland, Me.), prewarmed to 38.5° C. was added to each well. The plates were kept at 37° C. for a few minutes until several plates had accumulated and then centrifuged in plate carriers at 600×g for 20 minutes. In the centrifuge, cell monolayers formed prior to gelling of the agarose layer. The plates were incubated for 6 days at 37° C. in 5% $CO_2$ and stained by the addition of 0.05 mL of 50 μg/mL propidium iodide (Sigma Chemical Co.) in phosphate-buffered saline (pH 7.4) to each well. After 24 to 48 hours, the pink/orange fluorescence-stained microplaques were visualized by placing the plates on an 8,000 μW/cm² 304 nm UV light box (Fotodyne, Inc., New Berlin, Wis.). The plaques were counted at a magnification of between 20× and 25× through a stereomicroscope.

The results appear in Table 12.

TABLE 12

| Sample | Log Titer | Log Reduction |
|---|---|---|
| no QM | 5.5 | — |
| 3 µg/ml | 2.7 | -2.8 |
| 10 µg/ml | <0.7 | >-4.8 |
| 30 µg/ml | <0.3 | >-5.2 |
| 100 µg/ml | 1.75 | -3.75 |
| 150 µg/ml | <0.3 | >-5.2 |

It is clear from this example that QM inactivates cell-associated HIV, even at very low concentrations such as 10µg/ml and below.

EXAMPLE 9

This example sets forth the ability of two compound having a nucleic acid binding ligand and a mustard group, QM, and N-(2-chloroethyl)-N-ethyl-N'-(6-chloro-2-methoxy-9-acridinyl)-1,3-propanediamine dihydrochloride ("ICR-170") (commercially available from Polysciences Inc, Warrington, Pa.) to inactivate both cell-free and cell-associated HIV in the presence of red blood cells. The structure of ICR-170 is shown below.

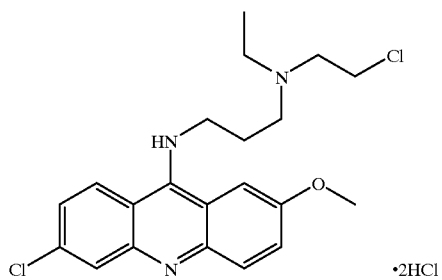

For the cell free HIV inactivation, 15 ml of PRBC was mixed with 5 ml Adsol for a final volume of 20 ml. Then ten 2 ml aliquots were added to 15 ml conical tubes. Varying doses of the two compounds were next added to the tubes. The stock compound solutions were both 1 mg/ml in saline, stored at 4° C. ICR-170 was in solution at this concentration. The following volumes of the two test compounds were added to the PRBC tubes: 20, 40, 80 or 160 µl; to produce final concentrations of the test compound of 10, 20, 40, or 80 µg/ml.

After addition of the compounds, the samples were incubated for 100 minutes at room temperature in the dark, with mixing every 30 minutes. Subsequently, the red blood cells were pelleted by spinning for 5 minutes at 2500 rpm. The supernatant was removed and NHSP was added so that the sample contained 15% NHSP. Samples were stored at 80° C.

Inactivation of cell-associated HIV was performed in a similar manner, with the following exceptions. H9 cells chronically infected with $HIV_{IIIB}$ were used. (H9/HTLV-III-B NIH 1983 Cat. #400). Cultures of these cells were maintained in high glucose DMEM supplemented with 2 mM L-glutamine, 200 units/mL penicillin, 200 µg/ml streptomycin, and 9% fetal bovine serum (Intergen Company, Purchase, N.Y.) For maintenance, the culture was split once a week, to a density of $3 \times 10^5$ to $4 \times 10^5$ cells/ml and about four days after splitting, 3.3% sodium bicarbonate was added as needed. For the inactivation procedure, the cells were used three days after they were split. The cells in a sample of this stock were counted on a Neubauer type Hemacytometer (commercially available from VWR Scientific, Greenbelt, Mo.), and found to have $1.07 \times 10^6$ cells/ml. An aliquot (18.7 ml, $20 \times 10^6$ cells) was pelleted and resuspended in 5 ml Adsol. This 5 ml of cell suspension was then added to 15 ml of PRBC. The sample was divided and compound was added as described above for the cell-free samples. The samples were incubated for 100 minutes, followed by the addition of 3 ml of a 1:1 mixture of NHSP and RPMI-1640 (commercially available from Irvine Scientific, Santa Ana, Calif.). Next, each sample was placed in a 15 ml tube containing 6 ml lymphocyte separation medium (LSM) (commercially available from Organon Teknika Corp., Durham, N.C.) and the tubes were spun at 1500 rpm for 30 minutes. The H9 cells, which separated into a distinct layer, were removed to another tube, mixed with 10 ml DMEM and spun at 2000 rpm for 5 minutes. The pellet was resuspended into 1 ml of 85% DMEM+15% FBS, and then transferred to a 2 ml sarstedt tube. The samples were also stored at 80° C.

The samples were titered using a microtiter plaque assay, as described in Example 8 for cell-free HIV and Example 9 for cell-associated HIV. The results appear in Table 13A (cell free) and 13B (cell associated), below.

TABLE 13A

Cell-free HIV Inactivation

| Compound | Concentration (µg/ml) | Log Titer pfu/ml | Log Reduction |
|---|---|---|---|
| QM | 0 | 5.7 | — |
|  | 10 | 3.9 | 1.8 |
|  | 20 | 3.0 | 2.7 |
|  | 40 | 0 | >4.3 |
|  | 80 | 0 | >4.3 |
| ICR-170 | 0 | 5.7 | — |
|  | 10 | 5.1 | 0.6 |
|  | 20 | 4.4 | 1.3 |
|  | 40 | 3.4 | 2.3 |
|  | 80 | 1.7 | 4.0 |

TABLE 13B

Cell-associated HIV Inactivation

| Compound | Concentration (µg/ml) | Log Titer | Log Reduction |
|---|---|---|---|
| QM | 0 | 5.5 | — |
|  | 10 | 4.4 | 1.1 |
|  | 20 | 3.6 | 1.9 |
|  | 40 | 2.5 | 3.0 |
|  | 80 | 2.4 | 3.1 |
| ICR-170 | 0 | 5.7 | — |
|  | 10 | 5.2 | 0.5 |
|  | 20 | 4.5 | 1.2 |
|  | 40 | 3.7 | 2.0 |
|  | 80 | 3.7 | 2.0 |

EXAMPLE 10

The above examples have established that QM has exceptional pathogen inactivation activity. In choosing an agent to decontaminate blood products for clinical testing or transfusion, it is also important to consider the effects of the method and compound used on blood product function. This example explores the short term effects of two compounds, one having a nucleic acid binding ligand and a mustard group, QM and chlorambucil on red blood cell function, as measured by potassium leakage and IgG binding to red blood cell surfaces. The structure of chlorambucil appears below.

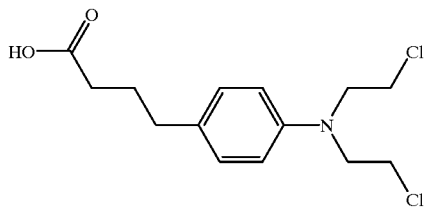

This example additionally compares the R17 inactivation activity, in red blood cells, of a compound having both a nucleic acid binding ligand and a mustard group (QM), with a compound having only a mustard group, and no nucleic acid binding ligand (chlorambucil).

Whole blood (20 ml) was transferred to a 50 ml conical tube and spun down at 1600 rpm for 9 minutes at room temperature. Plasma was removed (9 ml). Next, 10.9 logs/ml stock of R17 phage was diluted 1:20 with Adsol (24.4 ml Adsol+1.28 ml R17). The pelleted red blood cells were then resuspended to 30% Htc with 25.6 ml of the Adsol/R17 mixture. Aliquots (3 ml each) were transferred into 9 tubes on ice.

Each mustard was added to Adsol. Chlorambucil, commercially available from Aldrich Inc., Milwaukee, Wis., (5.8 mg) was added to 1.93 ml Adsol plus 5.85 μl 3M NaOH (undesolved material remained, and suspension was used in the experiment by swirling before addition. QM (2.9 mg) was added to 0.967 ml Adsol (again, material remained in suspension). The mustards were immediately added to the blood, at volumes set forth in Table 14, below, and mixed by inversion.

TABLE 14

| Sample | Contents | Volume Mustard |
|---|---|---|
| 1 | control | none |
| 2 | 10 μg/ml Chlorambucil | 10 μl |
| 3 | 30 μg/ml Chlorambucil | 30 μl |
| 4 | 100 μg/ml Chlorambucil | 103 μl |
| 5 | 300 μg/ml Chlorambucil | 333 μl |
| 6 | 10 μg/ml Quinacrine | 10 μl |
| 7 | 30 μg/ml Quinacrine | 30 μl |
| 8 | 100 μg/ml Quinacrine | 103 μl |
| 9 | 300 μg/ml Quinacrine | 333 μl |

Extracellular potassium levels were measured approximately one hour after treatment using a Ciba Corning 614 $K^+/Na^+$ Analyzer (commercially available from Ciba Corning Diagnostics Corp., Medfield, Mass.). The remaining samples were incubated overnight at 4° C. After incubation, 0.2 ml of each sample was removed for R17 assay and spun in a microfuge for 1 min. Supernatant was then removed for phage assay.

Figure 6:
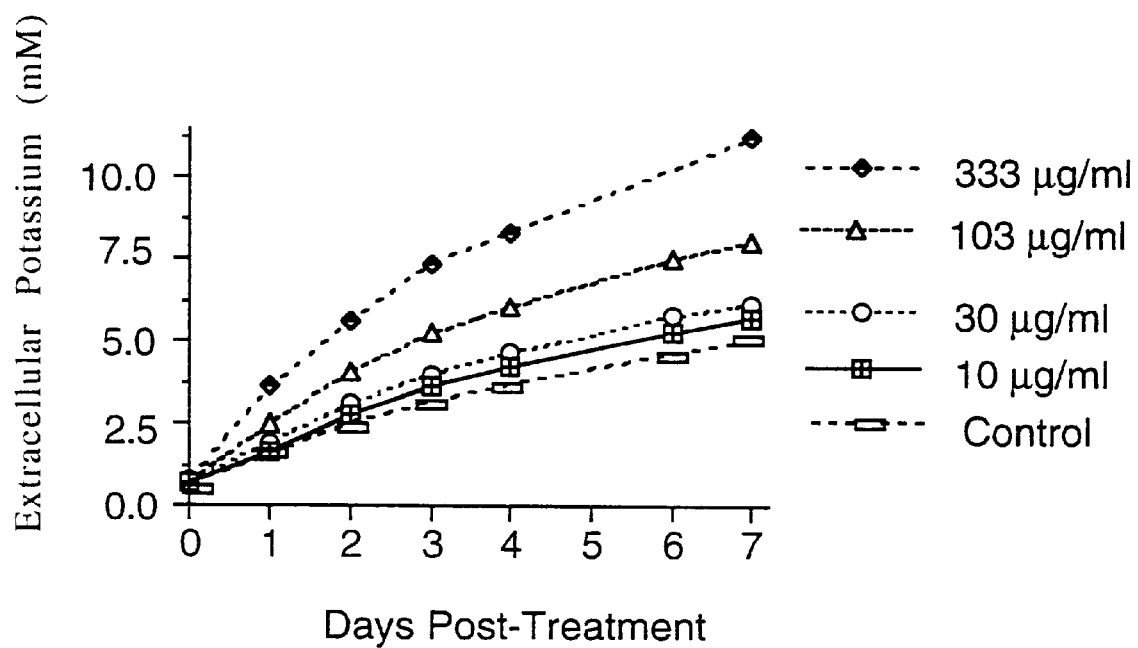
FIG. 6 is a graph showing the effects of quinacrine mustard at varying concentrations on extra-cellular potassium levels.

Potassium levels on remaining samples were measured and the samples were stored at 4° C. Potassium measurements were repeated daily for one week or untol significant differences were observed. Extracellular potassium data appears in Table 15, and FIG. 6. IgG binding in the samples was measured using Baxter Unival Anti-Human Globulin Anti-IgG for Direct Antiglobulin Test and Baxter Coombs control Cells for Quality Control of Anti-Human Globulin Test (both available from Baxter Healthcare Corporation, Deerfield, Ill.). The results of IgG Binding as measured by $FACS_{can}$™ (Becton Dickinson, Mountain View, Calif.) appear in Table 16:

R17 was completely inactivated at all concentrations of QM ($\geq$8.4 logs/ml). However, little or no inactivation ($\leq$0.4 logs) was observed for Chlorambucil, up to a concentration of 300 μg/ml.

TABLE 15

| Sam- | Extracellular Potassium (mM) | | | | | | |
|---|---|---|---|---|---|---|---|
| ple | Day 0 | Day 1 | Day 2 | Day 3 | Day 4 | Day 6 | Day 7 |
| 1 | 0.70 | 1.59 | 2.51 | 3.16 | 3.71 | 4.63 | 5.01 |
| 2 | 0.76 | 1.59 | 2.45 | 3.18 | 3.72 | 4.57 | 4.94 |
| 3 | 0.69 | 1.56 | 2.40 | 3.16 | 3.72 | 4.69 | 5.03 |
| 4 | 0.72 | 1.74 | 2.43 | 3.18 | 3.76 | 4.73 | 5.12 |
| 5 | 0.72 | 1.71 | 2.58 | 3.31 | 3.92 | 4.89 | 5.36 |
| 6 | 0.73 | 1.65 | 2.76 | 3.64 | 4.26 | 5.30 | 5.69 |
| 7 | 0.76 | 1.94 | 3.08 | 4.00 | 4.63 | 5.76 | 6.15 |
| 8 | 0.78 | 2.48 | 4.05 | 5.23 | 6.06 | 7.50 | 8.02 |
| 9 | 0.82 | 3.61 | 5.59 | 7.37 | 8.32 | >10 | 11.20 |

TABLE 16

| Sample | 1 | 2 | 3 | 4 | 5 | 6 | 7 | 8 | 9 |
|---|---|---|---|---|---|---|---|---|---|
| Median Fluorescence | 3.43 | 3.31 | 3.37 | 3.31 | 3.62 | 5.00 | 7.77 | 15.8 | 48.7 |

Chlorambucil did not alter potassium leakage or IgG binding of red cells. QM showed significant anti-viral activity and only induced slight changes in red blood cell function under the conditions of this experiment. Significant red blood cell damage was only detected at levels far higher than that required to inactivate R17.

EXAMPLE 11

Example 10 showed that QM was able to inactivate R17 in red blood cells under conditions where potassium leakage and surface IgG binding were negligible. This example is designed to further these observations by looking more extensively at red blood cell function after treatment with varying levels of QM. Specifically, this example looks at the effects of QM treatment on red blood cell function after storage under conditions that closely mimic those in a blood bank.

A packed red blood cell unit, approximately 1 day old, was obtained from Sacramento Blood Center. The cells were resuspended and approximately 200 ml was transferred to a sterile container. R17 (0.2 ml) in LB was added and the sample was mixed. Next the unit was divided into 6–30 ml aliquots in sterile conical centrifuge tubes on ice. The remaining packed red blood cells were stored in the bag at 4° C.

QM (3.2 mg) was mixed with ice cold Adsol (1.6 ml) to make a 2.0 mg/ml suspension. Aliquots of the QM suspension were added to the cells as set forth in Table 17. The samples were mixed thoroughly by gentle inversion and transferred to Fenwal transfer packs (Baxter/Fenwal, Ill.) for storage at 4° C.

TABLE 17

| Sample | Final Concentration of QM (μg/ml) | Volume of QM |
|---|---|---|
| 1 | 0 | 0 |
| 2 | 2.5 | 37.5 μl |

TABLE 17-continued

| Sample | Final Concentration of QM (μg/ml) | Volume of QM |
|---|---|---|
| 3 | 5 | 75 μl |
| 4 | 10 | 0.15 ml |
| 5 | 20 | 0.30 ml |
| 6 | 40 | 0.60 ml |

The following measurements of cell function were taken. 1) Potassium levels were determined daily for one week and weekly thereafter, using the Ciba Corning 614 $K^+/Na^+$ analyzer (commercially available from Ciba Corning, Mass.). 2) Adenosine-5'-triphosphate (ATP) and 2,3-diphosphoglyceric acid (2,3-DPG) were measured the first day after treatment and weekly thereafter. ATP was measured using a Sigma ATP Kit, commercially available from Sigma, St. Louis Mo., following Sigma Procedure No. 366-UV hereby incorporated by reference. 2,3-DPG was measured using the 2,3-DPG Kit, commercially available from Sigma, St. Louis, Mo. 3) IgG binding to the red blood cell surface was measured after day 1 and week 1, using the Baxter Unival Anti-Human Globulin Anti-IgG for Direct Antiglobulin Test and Baxter Coombs Control Cells for Quality Control of Anti-Human Globulin Test, commercially available from Baxter Healthcare, Inc., Deerfield, Ill.

Figure 7:
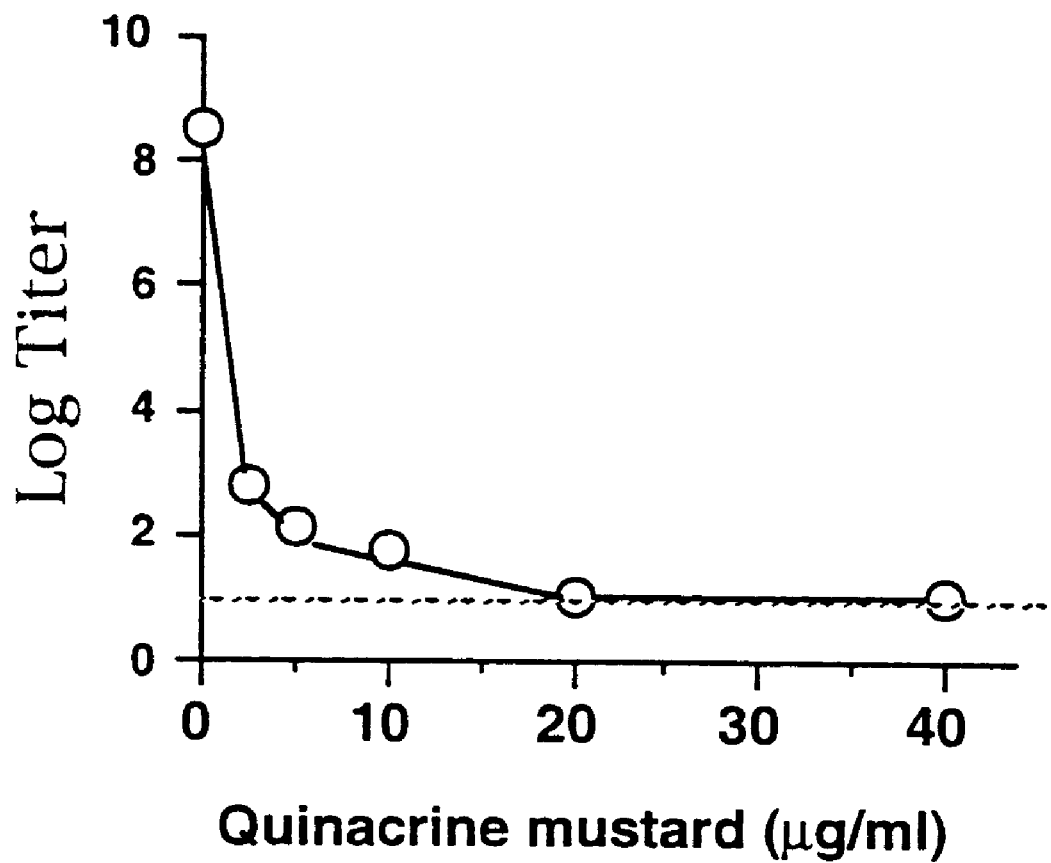
FIG. 7 is a graph showing the reduction in titer of R17 treated with varying concentrations of quinacrine mustard; the horizontal dotted line represents the limit of detection of the assay used.

The results for R17 inactivation appear in FIG. 7. The results for red blood cell function appear in Tables 18A–18D.

TABLE 18A

| QM Concentration | $K^+$ Day 1 | $K^+$ Day 2 | $K^+$ Day 7 | $K^+$ Day 8 | $K^+$ Day 9 | $K^+$ Day 16 |
|---|---|---|---|---|---|---|
| control | 7.41 | 7.41 | 13.20 | 12.96 | 15.32 | 31.72 |
| 2.5 μg/ml | 7.42 | 7.42 | 12.90 | 13.64 | 15.86 | 31.76 |
| 5 μg/ml | 7.24 | 7.24 | 13.28 | 14.82 | 15.18 | 32.96 |
| 10 μg/ml | 7.24 | 7.24 | 13.06 | 15.16 | 14.68 | 31.64 |
| 20 μg/ml | 7.00 | 7.00 | 12.90 | 15.38 | 14.44 | 31.36 |
| 40 μg/ml | 6.95 | 6.95 | 12.88 | 12.44 | 15.44 | 30.92 |

TABLE 18B

| QM Concentration | ATP (mM) Day 1 | ATP (mM) Day 9 | ATP (mM) Day 16 |
|---|---|---|---|
| control | 0.77 | 0.80 | 0.75 |
| 2.5 μg/ml | 0.78 | 0.80 | 0.74 |
| 5 μg/ml | 0.78 | 0.81 | 0.73 |
| 10 μg/ml | 0.76 | 0.81 | 0.73 |
| 20 μg/ml | 0.78 | 0.80 | 0.73 |
| 40 μg/ml | 0.76 | 0.80 | 0.72 |

TABLE 18C

| QM Concentration | 2,3-DPG Day 1 | 2,3-DPG Day 9 | 2,3-DPG Day 16 |
|---|---|---|---|
| control | 2.20 | 0.77 | 0.89 |
| 2.5 μg/ml | 2.20 | 0.88 | 0.10 |
| 5 μg/ml | 2.35 | 0.97 | 0.28 |
| 10 μg/ml | 2.06 | 1.11 | 0.34 |
| 20 μg/ml | 2.63 | 1.43 | 1.36 |
| 40 μg/ml | 2.09 | 1.04 | 0.11 |

TABLE 18D

| QM Concentration | mean FL Day 1 | median FL Day 1 | mean FL Day 9 | median FL Day 9 | mean FL Day 16 | median FL Day 16 |
|---|---|---|---|---|---|---|
| control | 4.41 | 4.1 | 4.41 | 4.1 | 4.41 | 4.1 |
| 2.5 μg/ml | 4.77 | 4.45 | 4.77 | 4.45 | 4.77 | 4.45 |
| 5 μg/ml | 4.79 | 4.45 | 4.79 | 4.45 | 4.79 | 4.45 |
| 10 μg/ml | 4.96 | 4.7 | 4.96 | 4.7 | 4.96 | 4.7 |
| 20 μg/ml | 5.73 | 5.19 | 5.73 | 5.19 | 5.73 | 5.19 |
| 40 μg/ml | 6.31 | 6.04 | 6.31 | 6.04 | 6.31 | 6.04 |

Under conditions of effective R17 inactivation in packed red blood cells, there are no significant effects on potassium-leakage, ATP content or 2,3-DPG content, and only modest effects on IgG binding to RBCs.

EXAMPLE 12

This example evaluates QM to determine whether it is mutagenic in the Ames test, a well known assay for mutagenicity. While mustards are proving to be effective compounds for pathogen inactivation, they are also considered potential mutagens. This example shows that blood treated with QM does not exhibit significant mutagenic action, particularly after an incubation period. Thus, the compounds of the present invention have exceptional pathogen inactivation efficiency while displaying only minimal mutagenicity.

In this example QM was tested for its mutagenicity using an Ames assay. The mutagenicity was tested under four conditions: QM incubated overnight in water, QM added to red blood cells and immediately plated; QM added to red blood cells, incubated overnight at 4° C. and then plated; and QM added to red blood cells, incubated 4 hours at 4° C., then mixed with Amberlite XAD-16™ and incubated overnight before plating.

First, the solubility of QM in red blood cells was determined. 10 mg/ml QM was diluted 10-fold and 100-fold into red blood cells and the solubility was observed. To obtain a 1.0 mg/ml solution, 20 μl of the 10 mg/ml QM solution was combined with 180 μl of the 50% Htc red blood cells. This stock contained definite particles. Next a 0.3 mg/ml concentration was tested by combining 20 μl of 3.0 mg/ml QM and 180 μl of 50% Htc red blood cells. There was evidence of precipitating out of solution with the 3 mg/ml stock. Finally, 20 μl of the 1.0 mg/ml stock was mixed with 180 μl of packed red blood cells. The 1.0 mg/ml stock appeared clear. The 3 mg/ml stock was chosen as the highest concentration, thus 0.3 mg/ml in red blood cells and 30 μg/plate are the upper concentration limits in this experiment.

Preparation of these three test mixtures was as follows. A 10 mg/ml solution of QM in DMSO was diluted to 1.0 mg/ml (60 μl of QM solution added to 0.54 ml DMSO). A 50% Htc red blood cell solution was prepared by spinning down 10 ml of a packed red cell unit at 1600 rpm for 9 minutes. Supernatant was removed and the cell pellet was resuspended in an equal volume of Adsol. Htc was then confirmed on a Model F800 Sysmex cell counter (Toa Medical Electronics, Kobe, Japan). Thirteen 0.9 ml aliquots of RBC solution were then placed in test tubes. Four different stock solutions of QM were prepared because the compound may precipitate out of solution at concentrations as low as 3 mg/ml. Stock solutions at varying concentrations were prepared by making the following dilutions of a 1.0 mg/ml solution: 150 μl of a 1.0 mg/ml QM solution+350 μl DMSO to produce a 0.3 mg/ml solution; 40 μl of a 1.0 mg/ml QM solution+360 μl DMSO to produce a 0.1 mg/ml solution; 15 μl of a 1.0 mg/ml QM solution+485 μl DMSO to produce a 0.03 mg/ml solution. To the first tube, 100 μl DMSO was added and the tube was placed on a 4° C. shaker (25 rpm, Orbital Shaker, commercially available from VWR Scientific, Greenbelt, Mo.) for overnight incubation. Tubes 2–5 were shaken overnight as well, then 100 μl aliquots of each QM solution was diluted into the tubes just before addition to the Ames strains. To tubes 6–9 was added 100 μl of each QM solution. The tubes were then incubated overnight at 4° C. on the shaker. Finally, 100 μl of each QM solution was also added to tubes 10–13, which were then incubated on the shaker for 4 hours. Subsequently, 0.1 g of a polymeric adsorbent material, Amberlite XAD 16™ (commercially available from Sigma, Saint Louis, Mo.), was added to each of tubes 10–13 and the incubation was continued overnight. The final contents of each tube, and the stock QM solutions used, are listed in Table 19, below.

TABLE 19

| SAMPLE NUMBER | CONTENTS | QM STOCK SOLUTION |
|---|---|---|
| 1 | RBC + DMSO | none |
| 2 | RBC + 0.003 mg/ml QM | 0.03 mg/ml |
| 3 | RBC + 0.01 mg/ml QM | 0.1 mg/ml |
| 4 | RBC + 0.03 mg/ml QM | 0.3 mg/ml |
| 5 | RBC + 0.1 mg/ml QM | 1 mg/ml |
| 6 | RBC + 0.003 mg/ml QM | 0.03 mg/ml |
| 7 | RBC + 0.01 mg/ml QM | 0.1 mg/ml |
| 8 | RBC + 0.03 mg/ml QM | 0.3 mg/ml |
| 9 | RBC + 0.1 mg/ml QM | 1 mg/ml |
| 10 | RBC + 0.003 mg/ml QM | 0.03 mg/ml |
| 11 | RBC + 0.01 mg/ml QM | 0.1 mg/ml |
| 12 | RBC + 0.03 mg/ml QM | 0.3 mg/ml |
| 13 | RBC + 0.1 mg/ml QM | 1 mg/ml |

In a separate experiment, samples of QM in water were prepared as follows. Sample tubes were labeled and 0.5 ml phosphate buffer was added to each one. Then various dilutions of a stock solution of QM (1 mg/ml) were added to five of the tubes. For 100 μg/plate –1.4 ml stock solution; for 30 μg/plate –0.42 ml stock+0.98 ml $H_2O$; for 10 μg/plate –0.14 ml stock+1.26 ml $H_2O$; for 3 μg/plate –0.042 ml stock+1.358 ml $H_2O$; for 1 μg/plate –0.014 ml stock+1.386 ml $H_2O$. A control was also prepared using only $H_2O$.

The procedures used for the Salmonella mutagenicity test as described in detail by Maron and Ames were followed exactly. Maron, D. M. and B. N. Ames, Mutation Research 113: 173 (1983). A brief description for each procedure is given here. The tester strains TA97a, TA98, TA100, TA102, TA1537 and TA1538 were obtained from Dr. Ames. TA97a, TA98, TA1537 and TA1538 are frame shift tester strains. TA100 and TA102 are base-substitution tester strains. Upon receipt each strain was cultured under a variety of conditions to confirm the genotypes specific to the strains.

The standard Salmonella tester strains used in this study require histidine for growth since each tester strain contains a different type of mutation in the histidine operon. In addition to the histidine mutation, these tester strains contain other mutations, described below, that greatly increase their ability to detect mutagen.

Histidine Dependence: The requirement for histidine was tested by streaking each strain first on a minimal glucose plate supplemented only with biotin and then on a minimal glucose plate supplemented with biotin and histidine. All strains grew only on the histidine/biotin supplemented plates, confirming a histidine requirement.

rfa Mutation: A mutation which causes partial loss of the lipopolysaccharide barrier that coats the surface of the bacteria thus increasing permeability to large molecules was confirmed by exposing a streaked nutrient agar plate coated with the tester strain to crystal violet. First 100 μL of each culture was added to 2 mL of molten minimal top agar and poured onto a nutrient agar plate. Then a sterile filter paper disc saturated with crystal violet was placed at the center of each plate. After 16 hours of incubation at 37° C. the plates were scored and a clear zone of no bacterial growth was found around the disc, confirming the rfa mutation.

uvrB Mutation: Three strains used in this study contain a deficient UV repair system (TA97a, TA98, TA100, TA1537 and TA1538). This trait was tested for by streaking the strains on a nutrient agar plate, covering half of the plate, and irradiating the exposed side of the plate with germicidal lamps. After incubation growth was only seen on the side of the plate shielded from UV irradiation.

R-factor: The tester strains (TA97a, TA98, TA100, and TA102) contain the pKM101 plasmid that increases their sensitivity to mutagens. The plasmid also confers resistance to ampicillin to the bacteria. This was confirmed by growing the strains in the presence of ampicillin.

pAQ1: Strain TA102 also contains the pAQ1 plasmid that further enhances its sensitivity to mutagens. This plasmid also codes for tetracycline resistance. To test for the presence of this plasmid TA102 was streaked on a minimal glucose plate containing histidine, biotin, and tetracycline. The plate was incubated for 16 hours at 37° C. The strain showed normal growth indicating the presence of the pAQ1 plasmid.

The same cultures used for the genotype testing were again cultured and aliquots were frozen under controlled conditions. The cultures were again tested for genotype to confirm the fidelity of the genotype upon manipulation in preparing the frozen permanents.

The first tests done with the strains were to determine the range of spontaneous reversion for each of the strains. With each mutagenicity experiment the spontaneous reversion of the tester strains to histidine independence was measured and expressed as the number of spontaneous revertants per plate. This served as the background controls. A positive mutagenesis control was included for each tester strain by using a diagnostic mutagen suitable for that strain (2-aminofluorene at 5 mg/plate for TA98; sodium azide at 1.5 mg/plate for TA100; 9-aminoacridine for TA 1537).

For all experiments, the pre-incubation procedure was used. In this procedure one vial of each tester strain was thawed and tubes were prepared for each strain, containing 20 μL of the culture and 6 mL of Oxoid Nutrient Broth #2. This solution was allowed to shake for 10 hours at 37° C. In the pre-incubation procedure, for each tester strain used to evaluate the test solution, 0.1 mL of the overnight culture was added to each of 13 sterile test tubes. To each of the tubes, 0.1 mL of the test solution from tubes 1–13 was added. This was also performed on the samples containing QM in water only. Then 0.5 mL of 0.2 M sodium phosphate buffer, pH 7.4 was added. The 0.7 mL mixture was vortexed and then pre-incubated while shaking for 20 minutes at 37° C. After shaking, 2 mL of molten top agar supplemented with histidine and biotin were added to the 0.7 mL mixture and immediately poured onto a minimal glucose agar plate (volume of base agar was 20 mL). The top agar was allowed 30 minutes to solidify and then the plates were inverted and incubated for 44 hours at 37° C. After incubation, the number of revertant colonies on each plate was counted.

Figure 8:
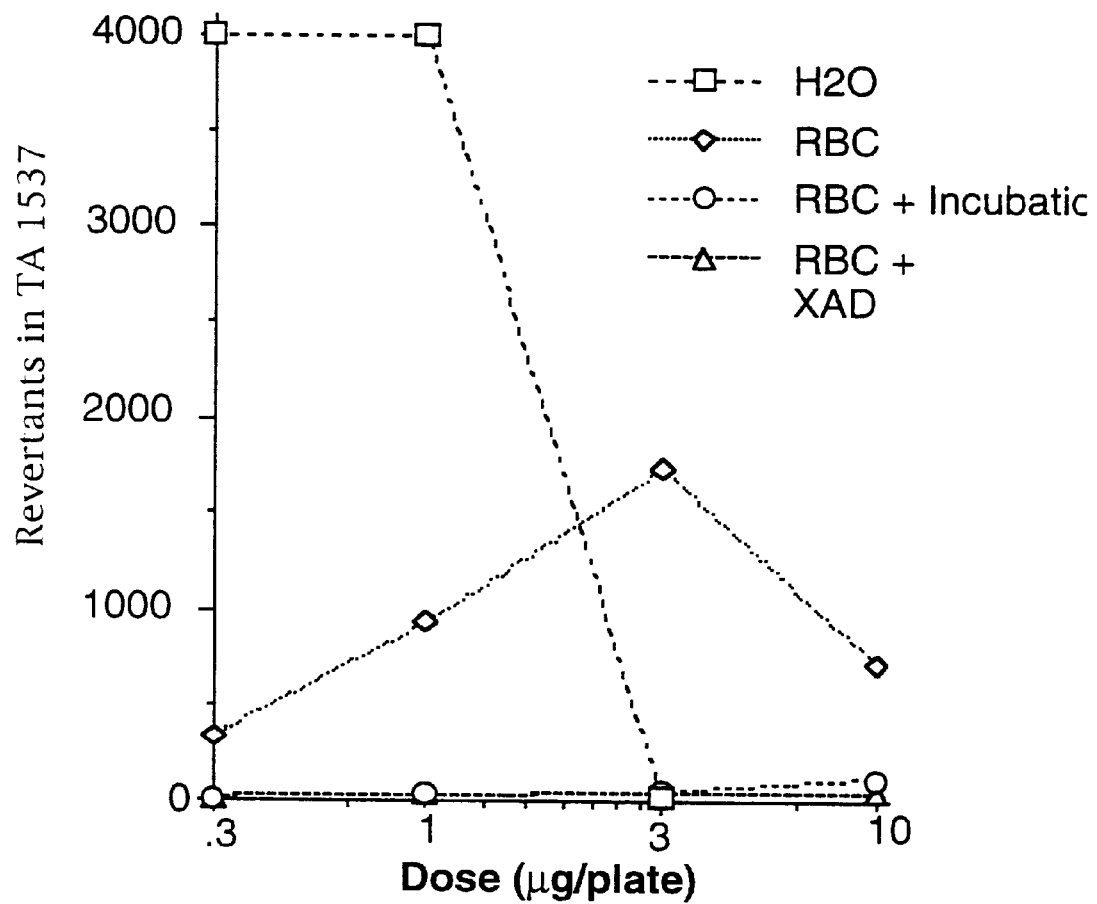
FIG. 8 is a graph showing the activity of quinacrine mustard, after incubation in red blood cells, with or without the presence of Amberlite XAD-16™, in an Ames assay using strain TA 1537.
Figure 9:
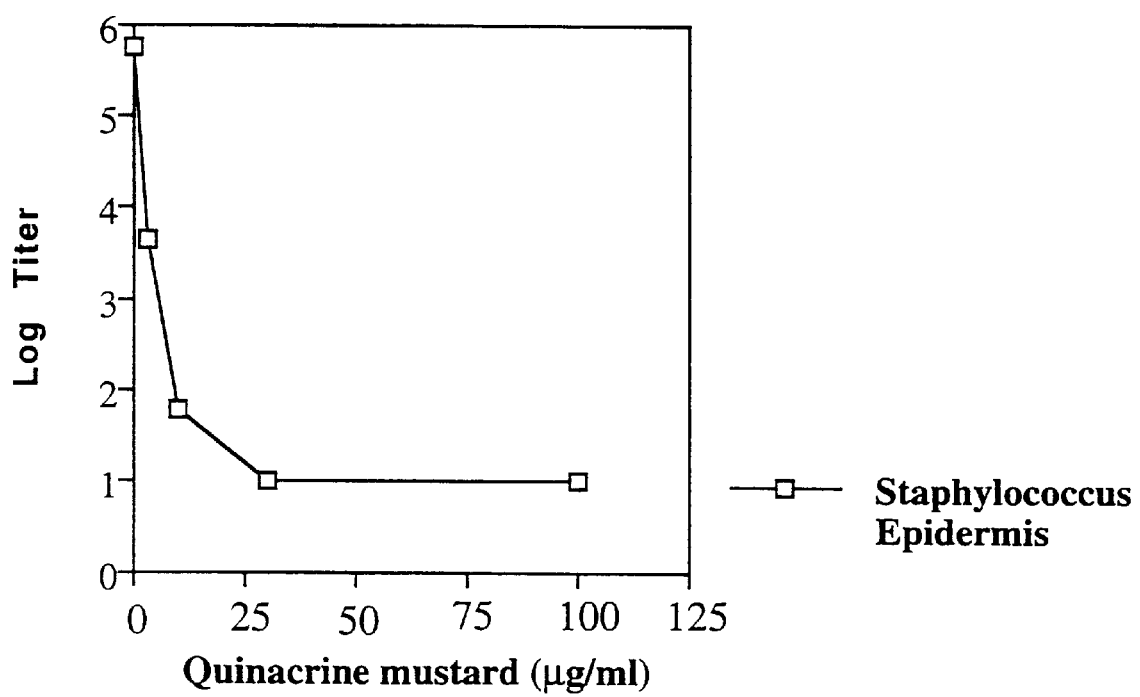
FIG. 9 is a graph showing the inactivation of a bacterial strain, Staphylococcus Epidermis, using quinacrine mustard at varying concentrations.

The results appear in FIG. 8. Although the QM registered a positive response in the Ames test without incubation in red blood cells and in water, an overnight incubation in red blood cells significantly reduced the level of revertants, as did an incubation with adsorbent material. A parallel experiment was performed using an activated charcoal adsorbent material, Hemosorba (commercially available from Asahi Medical Corp., Tokyo, Japan.) The results, which are not shown, were similar to the results using Amberlite XAD 16™.

EXAMPLE 13

As discussed above, a method of decontaminating clinical samples would be most useful if while it decontaminated samples, it did not significantly effect the results of the clinical tests themselves. This example compares results of a common blood chemistry panel for samples treated by methods of the present invention to untreated samples.

Solutions of QM and ICR-170 (2 mg/ml) were prepared in saline. The QM was almost completely dissolved, and ICR-170 remained a suspension. Next, human whole blood was drawn and 10 ml aliquots were placed in eight tubes. QM or ICR-170 was added to six of the tubes in aliquots of 100, 200, or 400 µl, to reach final concentrations of the compounds of either 20, 40, or 80 µg/ml. Saline was added to the remaining two tubes, in aliquots of 100 or 400 µl, to prepare control samples. The samples were then allowed to clot for 30 minutes, followed by 20 minutes on a centrifuge at 1000 rpm. The separated serum was then transferred to labeled plastic tubes and tested in a panel of 24 common clinical chemistry tests.

The results appear below, in Table 20. Neither QM nor ICR-170 had a significant effect on the results of any of the panel of 24 clinical chemistry tests. Lactate dehydrogenase and GGT exhibited a small drop in the sample containing the highest concentration of ICR-170. Clearly, the methods of the present invention do not interfere significantly with clinical testing of blood samples.

TABLE 20

| TEST | 100 µl saline | 400 µl saline | 20 µg/ml QM | 40 µg/ml QM | 60 µg/ml QM | 20 µg/ml ICR170 | 40 µg/ml ICR170 | 60 µg/ml ICR170 |
|---|---|---|---|---|---|---|---|---|
| Glucose | 95 | 92 | 93 | 93 | 90 | 94 | 92 | 90 |
| BUN | 17 | 17 | 17 | 17 | 17 | 17 | 17 | 17 |
| Creatinine | 1.1 | 1.1 | 1.1 | 1.2 | 1.1 | 1 | 1.1 | 1.1 |
| Bun/Creat. ratio | 15 | 15 | 15 | 14 | 15 | 17 | 15 | 15 |
| Sodium | 143 | 143 | 138 | 144 | 146 | 143 | 144 | 144 |
| Potassium | 4 | 3.9 | 4 | 3.9 | 3.9 | 4 | 4.1 | 4.1 |
| Chloride | 104 | 106 | 104 | 106 | 107 | 103 | 104 | 103 |
| Magnesium | 1.7 | 1.6 | 1.6 | 1.6 | 1.6 | 1.7 | 1.6 | 1.5 |
| Calcium | 9.3 | 8.8 | 9.3 | 8.8 | 9 | 9.4 | 9.2 | 9.1 |
| Phosphorous inorganic | 4.3 | 3.9 | 4.1 | 4.1 | 4.1 | 4.3 | 4.3 | 4.1 |
| protein, total | 7.3 | 7.1 | 7.4 | 7.3 | 7.1 | 7.3 | 7.3 | 7.1 |
| albumin | 4.6 | 4.5 | 4.6 | 4.6 | 4.4 | 4.6 | 4.6 | 4.4 |
| globulin, total | 2.7 | 2.6 | 2.8 | 2.7 | 2.7 | 2.7 | 2.7 | 2.7 |
| A/G ratio | 1.7 | 1.7 | 1.6 | 1.7 | 1.6 | 1.7 | 1.7 | 1.6 |
| billirubin | 0.6 | 0.6 | 0.6 | 0.6 | 0.6 | 0.6 | 0.6 | 0.6 |
| alk | 55 | 50 | 48 | 50 | 51 | 54 | 51 | 47 |
| LDH | 136 | 134 | 121 | 125 | 138 | 129 | 138 | 151 |
| GGT | 23 | 21 | 22 | 22 | 22 | 23 | 20 | 16 |
| AST | 17 | 16 | 18 | 16 | 16 | 16 | 17 | 16 |
| ALT | 20 | 19 | 17 | 19 | 18 | 19 | 19 | 19 |
| Uric Acid | 5.6 | 5.3 | 5.5 | 5.4 | 5.4 | 5.7 | 5.6 | 5.5 |
| Iron | 119 | 107 | 117 | 113 | 115 | 119 | 122 | 120 |
| Triglycerides | 164 | 152 | 159 | 158 | 158 | 161 | 150 | 156 |
| Cholesterol | 234 | 221 | 227 | 226 | 223 | 231 | 231 | 223 |

EXAMPLE 14

This example describes the inactivation of bacterial pathogens of biological compositions using methods of the present invention. The following experiment was performed to support that the methods of the present invention can be used to inactivate bacterial pathogens. In this example, the decontamination methods of the present invention were applied to inactivate *Staphylococcus epidermis*.

An overnight culture of the organism was made by inoculating 3 ml of LB broth from a motility stab. This was maintained at 35° C. and 1.0 ml of it was used to inoculate 9 ml of LB broth in a 15 ml conical tube. A sample (1 ml) was taken for an OD600 reading. To a tube, 5 ml of LB broth was added. Then 50 µl of $10^8$ cfu/ml *S. epidermis* was added. Aliquots of the sample (1 ml each) were placed in 5 tubes. These were treated with either 0, 3, 10, 30, or 100 µg/ml of QM. A 2 mg/ml stock of QM in ddH$_2$O was added in the following amounts to produce the desired concentrations: 0 µl, 1.5 µl, 5 µl, 15 µl, and 50 µl. The samples were incubated on ice for three hours.

After incubation, bacteria was quantified by plating 0.1 ml of serial 10-fold dilutions in LB broth onto 100 mm petri dishes containing agar. After 24 hr. incubation at 35° C., colonies were counted and bacterial concentration was calculated on a per ml basis. The results, which appear in FIG.

9, show that QM at >10 μg/ml inactivates *S. epidermis* to the level of detection of this assay.

EXAMPLE 15

If a decontaminated blood product is to have value as an in vivo therapy, the blood product must retain some efficacy after the decontamination process. One way to confirm the efficacy of a particular sample of red blood cells is to ensure that they are not cleared by the recipient's body significantly sooner than normal red blood cells when transfused into a mammal. In this example, packed red blood cells are treated with compounds having a nucleic acid binding ligand and a mustard group, according to the methods of the present invention, transfused into mice, and tracked for post transfusion survival.

Blood was drawn from 8 Balb/c mice using an anticoagulant (containing citrate, ethalene diamine tetraacetic acid, prostaglandin E1 and theophyllin) for a total of 12 ml (8 ml whole blood and 4 ml anticoagulant). An equivalent volume of Adsol was added and the sample was centrifuged at 2000 rpm for 5 minutes. The supernatant was removed and saved as "washed solution." The red blood cell pellet was resuspended in Adsol to make a 50% Htc solution. Three 1.5 ml aliquots were transferred to 14 ml round bottom polypropylene tubes.

Next, 1 mg/ml solutions of two compounds, QM and ICR-170, were prepared in saline. The compounds were added to the three polypropylene tubes as follows: tube 1 received no treatment (120 μl of saline was added); tube 2 received 120 μl of the 1 mg/ml solution of QM for a final concentration of 80 μg/ml; tube 3 120 μl of the 1 mg/ml solution of ICR-170, for a final concentration of 80 μg/ml.

The samples were then incubated for 2 hours at 4° C. Cells were washed three times, each time by adding 6 ml Adsol to each tube and spinning the samples at 1800 rpm for 5 minutes. After the final wash, the pellet was resuspended in Adsol buffer to a concentration of 4×10⁶ cells/μl. 50 μl of each sample was removed for an unstained control.

The remaining cells were then stained with PKH26 dye. From a 1 mM PKH26 stock, 120 μl was removed and diluted with 8 ml diluent A to create a working solution of 15.7 μM PKH26. This solution was stored in the dark until use. To each 2 ml of cells, 2 ml of PKH26 dye was added. The samples were mixed gently and incubated for 5 minutes at room temperature in the dark. The cells were remixed after 2.5 minutes. After another 5 minute incubation, 2 volumes of the reserved "washed solution" was added to stop the staining reaction. The cells were centrifuged at 1800 rpm for 5 minutes to pellet and the supernatant was removed. The cells were then washed 3 times with Adsol buffer, as before. After the final wash, the sample volume was restored to 1 ml with Adsol. An aliquot of each sample was removed at this point for a positive stained control sample and counted on the Sysmex machine.

Swiss Webster mice were transfused with 0.2 ml of the labeled cells from each of samples 1–3 via tail vein injection. The mice were then weighed to calculate the blood volume. Blood volume is calculated as the animal weight in gm×0.06. Then, blood was drawn from the mice by retro-orbital venipuncture using heparin-EDTA coated capillary tubes at 1 hour, 24 hours, 2 more times during the first week, and one time weekly for 3 weeks. The eye bleeding samples were drained into isotonic solution before analysis.

Samples were analyzed on a FACScan™ at the FL2 (red fluorescent channel) with gating on the red cell population using forward and side scatter linear mode gates. The proportion of labeled cells in 100,000 total red cell gated events was determined.

TABLE 21

| SAMPLE | RECOVERY | LOSS PER DAY |
|---|---|---|
| Untreated | 90.3 ± 3.2 | 2.66% |
| QM | 80.8 ± 4.7 | 2.77% |
| ICR-170 | 86.0 ± 6.6 | 2.71% |

The results appear in Table 21. According to the results, regardless of treatment, treated cells survived in vivo as well as untreated control cells.

Some hemolysis of RBC was detected after labeling with PKH26. Thus, recoveries may be effected by the labeling technique. An alternative labeling technique was also used, as described. An activated biotin ester was injected via the tail vein of the Balb/c mice in order to label the red cells in vivo (each mouse received either a "low dose treatment"—0.1 mg injection on two successive days, or a "high dose treatment"—0.3 mg of biotin on three successive days). After treatment, low and high dose treatment cells with fluorescently tagged streptavidin were clearly distinguishable as detected by FACScan analysis. Low and high dose treatment cells were independently treated with 80 μg/ml of QM or ICR-170 as described above. After treatment, cells were washed, mixed with untreated cells that had been differentially labeled. Then three mice were transfused: one received untreated low and untreated high dose RBC, one received QM treated low and untreated high dose RBC, and one received ICR-170 treated low and untreated high RBC. Bleeding was performed as described above. The results appear in Table 22, below. Clearly, recovery of the treated cells is very similar to the untreated cells.

TABLE 22

| | % RECOVERY, LOW | % RECOVERY, HIGH |
|---|---|---|
| untreated | 96.2 | 93.5 |
| QM | 94.6 | 91.2 |
| ICR-170 | 93.1 | 90.4 |

EXAMPLE 16

This example sets forth the results of several screens for viral inactivation performed on compounds of the present invention which have acridine groups as their nucleic acid binding ligands. Descriptions of how these screens were performed are found in the above examples discussing R-17, cell free HIV and cell associated HIV. Table 24, below, shows the results. Activity is set forth by + for lowest, up to ++++ for complete inactivation (to the level of detection used).

TABLE 24

Anti-viral Activity of nucleic acid specific alkylating agents, ACRIDINE RING - LINKING CHAIN - N(CH2CH2Cl)2

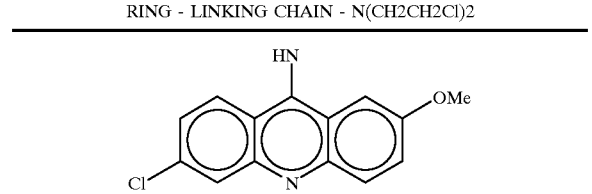

TABLE 24-continued

Anti-viral Activity of nucleic acid specific alkylating agents, ACRIDINE RING - LINKING CHAIN - N(CH2CH2Cl)2

Ring A

[structure: acridine with HN at top position]

Ring B

[structure: acridine with HN at top position]

Ring C

[structure: acridine with HN at top, NO2 substituent]

| Cmpd | Ring | linker | R17[a] | CA-HIV[b] | CF-HIV[b] |
|---|---|---|---|---|---|
| 2 | A | (CH2)2 | + | | |
| 3 | A | (CH2)3 | ++ | + | + |
| 4 | B | (CH2)3 | | + | + |
| 5 | A | (CH2)4 | ++++ | ++++ | +++ |
| 1 | A | CH(CH3)(CH2)3 | ++++ | +++ | +++ |
| 6 | A | (CH2)5 | ++++ | ++++ | +++ |
| 7 | B | (CH2)5 | | ++++ | ++++ |
| 8 | C | (CH2)5 | | + | ++ |
| 9 | A | (CH2)6 | ++++ | +++ | ++ |
| 10 | B | (CH2)6 | | ++++ | +++ |
| 11 | A | CH2CONH(CH2)3 | ++++ | +++ | ++ |
| 12 | A | CH(CH3)CONH(CH2)2 | ++++ | +++ | + |
| 13 | A | CH(CH3)CONH(CH2)3 | ++++ | +++ | + |

[a]++++ shows ≧6 log reduction at 5 uM compound;
[b]++++ shows ≧4 log reduction at 20 uM.

It is clear from these data that the acridine based compounds all have inactivation activity against all pathogens tested, including cell free, cell associated HIV and R-17.

Nucleic acid specific alkylating agents tested here have been prepared by methods described in [Peck, R. M., Preston, R. K., Creech, H. J., *J. Amer Chem. Soc* (1959) 81, 3984; Preston, R. K., Peck, R. M., Breuniger, E., R., Miller, A. J., Creech, H. J., *J. Med. Chem.* (1964) 7, 471]

EXAMPLE 17

This example describes the synthesis of a compound of the present invention, 5-[N,N-bis(2-chloroethyl)amino]methyl-8-methoxypsoralen hydrochloride (referred to throughout the text as "Compound 1").

Step 1: The synthesis of 5-Bromomethyl-8-methoxypsoralen.

To a solution of 2.69 g(12.3 mmol) of 8-methoxypsoralen (commercially available from Aldrich, Milwaukee, Wis.) in 135 mL of glacial acetic acid was added 11 mL of bromomethyl methyl ether. The solution was swirled, then left for three days at room temperature during which a white solid precipitated. The mixture was cooled in an ice bath and filtered. To the filtrate was added an additional 2.75 g (12.7 mmol) of 8-methoxypsoralen and 5 mL of BrCH$_2$OCH$_3$. After again sitting for three days, product isolation was repeated. The filter cakes were washed with cold glacial acetic acid, air dried and finally vacuum dried to give a total yield of 6.3 g (81%) of 5-bromomethyl-8-methoxypsoralen as a pale yellow solid. NMR (CDCl3): 4.33 (S, 3H), 4.88 (s, 2H), 6.52 (d, J=10 Hz, 1H), 6.95 (d, J=2 Hz, 1H), 7.77 (d, J==10 Hz, 1H).

Step 2: The synthesis of 5-[N,N-Bis-(2-hydroxyethyl)amino]methyl-8-methoxypsoralen.

5-Bromomethyl-8-methoxypsoralen (0.50g, 1.6mmol, from Step 1, above) and diethanolamine (2.56 mL, 27 mmol) were combined in 23 mL of absolute ethanol and refluxed for 10 hours. The solution was concentrated, then CHCl$_3$ (65 mL) was added to the residue. The organic layer was washed with 30, 30 and 10 mL of water sequentially and the combined aqueous solutions were back extracted with CHCl$_3$. The combined organic solutions were then extracted three times, each time with 7 mL of 1.2 N HCl. The combined acid solution was taken to pH5–6 with 10% aqueous NaOH and the resultant turbid solution was washed 4 times, each time with 20 mL of CHCl$_{13}$. This last organic solution was rinsed with 2×20 mL of brine, dried (Na$_2$SO$_4$) and concentrated to give 0.43 g (79%) of the aminediol, 5-[N,N-bis-(2-hydroxyethyl)amino]methyl-8-methoxypsoralen, melting point 121–122° C.; NMR (CDCl3): 2.71 (t, J=5 Hz, 4H), 3.61 (t, J=5 Hz, 4 H), 4.09 (s, 2H), 4.29 (s, 3H), 6.41 (d, J=10 Hz, 1H), 7.00 (d, J=2 Hz, 1H), 7.70 (d, J=2 Hz, 1H), 8.38 (d, J=10 Hz, 1H).

Step 3: 5-[N,N-Bis(2-chloroethyl)amino]methyl-8-methoxypsoralen hydrochloride.

5-[N,N-Bis(2-hydroxyethyl)amino]methyl-8-methoxypsoralen (0.030 g, 0.090 mmol) was dissolved in 1 ml thionyl chloride. It was covered with a serum cap with a small needle vent and allowed to stir for 3 days. The reaction mixture was stripped and the crude solid was recrystallized in isopropanol to give 5-[N,N-bis(2-chloroethyl)amino]methyl-8-methoxypsoralen hydrochloride (0.012 g, 32.4%) as an off-white solid, mp 158–162° C. $^1$HNMR (CD$_3$OD): 3.40 (t, J=6Hz, 4H), 3.86 (t, J=6Hz, 4H), 4.33 (s, 3H), 4.70 (s, 2H), 6.52 (d, J=10Hz, 1H), 7.28 (d, J=2Hz, 1H), 8.03 (d, J=2Hz, 1H), 8.48 (d, J=10Hz, 1H). The chemical shift appeared to be sensitive to trace acid present.

A portion of the above salt was partitioned between methylene chloride and aqueous NaHCO$_3$. The organic layer was again washed with aqueous bicarbonate, dried with brine, then dried with anhydrous Na$_2$SO$_4$ and evaporated to give the neutral amine; mass spectrum (EI, m/e): 371 (3), 369 (4), 230 (16), 229 (100), 214 (5), 201 (5), 186 (10) (obtained on a Shimadzu QP5000 GC/MS, with Rtx-5, 15m column, commercially available from Shimadzu Corporation, Kyoto, Japan).

EXAMPLE 18

This example describes a contemplated embodiment wherein red blood cells are treated by a method of the present invention. The standard blood product separation approach used presently in blood banks is as follows: three bags are integrated by flexible tubing to create a blood transfer set (e.g., commercially available from Baxter, Deerfield, Ill.). After blood is drawn into the first bag, the entire set is processed by centrifugation (e.g., Sorvall™ swing bucket centrifuge, Dupont), resulting in packed red cells and platelet rich plasma in the first bag. The plasma is expressed off of the first bag (e.g., using a Fenwall™ device for plasma expression), through the tubing and into the second bag. The first bag, containing packed red cells, is then detached.

In one embodiment of the decontamination approach of the present invention applied specifically to red blood cells, a compound having a nucleic acid binding ligand and a mustard group is introduced to the red blood cells (e.g. the compound may be present in the first bag before blood is drawn, or transferred to the first bag after centrifugation) and incubated. After incubation, the compound may be removed using an adsorbent material (e.g., a commercially available material, such as activated charcoal or an Amberlite resin). The adsorbent may be introduced directly into the bag containing the red blood cells, or the red blood cells may be passed through a scrub device which contains the adsorbent. The incubation, scrub, and any subsequent storage, may take place in a commercially available storage bag.

From the above, it should be evident that the present invention provides methods of decontamination of blood preparations intended for storage and in vivo use.

EXAMPLE 19

This example describes the synthesis of 8-[3-(Bis-2-chloroethyl) amino]propyloxypsoralen or 8-[N,N-Bis-(2-chloroethyl)-3-aminopropoxy]psoralen (compound 5)

STEP 1: 8-(3-Bromopropyloxy) psoralen 1,3-Dibromopropane (7 mL, 68.9 mmol) was added to a slurry of 8-hydroxypsoralen*ref (1.00 g, 4.95 mmol) in acetone (100 mL). After the addition of powdered $K_2CO_3$ (3.0 g, 21.7 mmol, 325 mesh), the mixture was refluxed for 6 h, allowed to cool to room temperature, and filtered to remove $K_2CO_3$. The salt was rinsed with $CH_2Cl_2$ and the combined filtrates were concentrated. To remove residual dibromopropane the precipitate was triturated with hexane, then recrystallized in methylcyclohexane to give 8-(3-bromopropoxy)psoralen (1.19 g, 56.9% yield), as a beige solid. $^1$H NMR ($CDCl_3$): d 2.41 (quintet, J=5.9 Hz, 2H), 3.78 (t, J=6.5 Hz, 2H), 4.64 (t, J=5.8 Hz, 2H), 6.38 (d, J=9.6 Hz, 1H), 6.82 (d, J=2.2 Hz, 1H), 7.71 (d, J=2.2 Hz, 1H), 7.78 (d, J=9.6 Hz, 1H).

STEP 2: 8-[3-(Bis-2-hydroxyethyl)amino]propyloxypsoralen 8-(3-Bromopropoxy)psoralen (0.500 g, 1.55 mmol) and diethanolamine (1.5 mL, 15.6 mmol) were refluxed in ethanol (20 mL) overnight. After rotovapping off the solvent, the resulting syrup was dissolved in $CH_2Cl_2$, washed with water several times, then brine, dried with anhydrous $Na_2SO_4$ and stripped of solvent to give 8-[3-(bis-2-hydroxyethyl)amino]propyloxypsoralen (0.499 g, 92.9% yield), as a brown syrup. $^1$H NMR ($CDCl_3$): d 2.04 (quintet, J=6.2 Hz, 2H), 2.72 (t, J=5.2 Hz, 4H), 2.91 (t, J=5.3 Hz, 4H), 4.54 (t, J=5.7 Hz, 2H), 6.38 (d, J=9.6 Hz, 1H), 6.82 (d, J=2.1 Hz, 1H), 7.39 (s,1H), 7.70 (d, J=2.1 Hz, 1H), 7.79 (d, J=9.5 Hz, 1H).

STEP 3: 8-[3-(Bis-2-chloroethyl)amino]propyloxypsoralen, or 8-[N,N-Bis-(2-chloroethyl)-3-aminopropoxy]psoralen (compound 5)

Thionyl chloride (0.030 mL, 0.41 mmol) was added dropwise to an ice bath chilled solution of 8-[3-(Bis-2-hydroxyethyl)amino]propyloxypsoralen (20.0 mg, 0.0575 mmol) and pyridine (0.016 mL, 0.21 mmol) in benzene (2 mL) and $CH_2Cl_2$ (2mL). The reaction mix was covered with a serum cap and allowed to stir overnight at rt, then stripped under reduced vacuum and partitioned between $CH_2Cl_2$ and 10% $NaHCO_3$. The organic layer was washed several times with aqueous $NaHCO_3$, then brine. After drying with anhydrous $Na_2SO_4$, solvent was rotovapped off to give 8-[3-(bis-2-chloroethyl)amino]propyloxypsoralen (14.0 mg, 57.8% yield), as a yellow solid. $^1$H NMR ($CDCl_3$): d 1.97 (app quintet J=6.3 Hz, 2H), 2.91 (app t, J=7.5 Hz, 6H), 3.55 (t, J=7.0 Hz. 4H), 4.58 (t, J=5.9 Hz, 2H), 6.37 (d, J=9.5 Hz, 1H), 6.82 (d, J=2.1 Hz, 1H), 7.37 (s, 1H), 7.70 (d, J=2.1 Hz, 1H), 7.77 (d, J=9.5 Hz, 1H).

8-[5-(Bis-2-chloroethyl)amino]pentyloxypsoralen (compound 6)

In the same manner as the foregoing, but using 1,5-dibromopentane in Step 1 in place of 1,3-dibromopropane, tcompound 6 is produced.

EXAMPLE 20

This example describes the synthesis of 5-[3-(Bis-2-chloroethyl) aminopyloxy]methyl-8-methoxypsoralen or 5-[N,N,-Bis-(2-chloroethy)-3-aminopropoxy]methoxpsoralen (compound 4)

STEP 1: 5-[(3-Hydroxy)-propyloxy]methyl-8-methoxypsoralen

5-Bromomethyl-8-methoxypsoralen@ (0.300 g, 0.970 mmol) and 1,3-propanediol (4 mL, 55.3 mmol) were refluxed in acetone (30 mL) for 3 days. The solvent was removed under reduced pressure and the residue was dissolved in $CH_2Cl_2$ and washed several times with water to remove excess diol. After preliminary drying with brine then anhydrous $Na_2SO_4$, the solvent was rotovapped off to give 5-[(3-hydroxy)-propyloxy]methyl-8-methoxypsoralen (0.194 g, 65.8% yield), as a yellow solid. $^1$H NMR ($CDCl_3$): d 1.86 (quintet, J=5.8 Hz, 2H), 3.68 (t, J=5.9 Hz, 2H), 3.75 (t, J=5.8 Hz, 2H), 4.30 s, 3H), 4.89 (s, 2H), 6.43 (d, J=9.9 Hz, 1H), 6.95 (d, J=2.2 Hz, 1H), 7.71 (d, J=2.2 Hz, 1H), 8.14 (d, J=9.9 Hz, 1H).

STEP 2: 5-[(3-Methanesulfonyl)propyloxy]methyl-8-methoxypsoralen

A solution of 5-(1-hydroxy-propoxy)methyl-8-methoxy psoralen (0.194 g, 0.637 mmol) in $CH_2Cl_2$ (4 mL) was chilled with an ice/water bath. Triethylamine (0.28 mL, 2.04 mmol) then methanesulfonyl chloride (0.15 mL,1.91 mmol) were added dropwise. The solution was allowed to warm to room temperature and stirred for 4–6 h. The reaction mixture was partitioned between $CH_2Cl_2$ and water and the organic layer was washed several times with water, then brine, and dried with anhydrous $Na_2SO_4$ and concentrated to give crude 5-[(3-methanesulfonyl)propyloxy]methyl-8-methoxypsoralen (0.266 g, 109% yield) which was used directly for the next step.

STEP 3: 5-[3-(Bis-2-hydroxyethyl)aminopropyloxy]methyl-8-methoxypsoralen

A solution of 5-[(3-methanesulfonyl)propyloxy]methyl-8-methoxypsoralen (0.266 g, 0.695 mmol) and diethanolamine (0.500 g, 4.76 mmol) were refluxed in acetonitrile (6 mL) overnight. After rotovapping off the solvent, the resulting syrup was dissolved in $CH_2Cl_2$, washed with water several times, then brine, dried with anhydrous $Na_2SO_4$ and stripped to give 5-[3-(Bis-2-hydroxyethyl)aminopropyloxy]methyl-8-methoxypsoralen (0.217 g, 82.8% yield), as a yellow solid. $^1$H NMR ($CDCl_3$): d 1.76 (quintet, J=6.1 Hz, 2H), 2.60–2.67 (m, 6H), 3.55–3.63 (m, 6H), 4.29 (s, 3H), 4.88 (s, 2H), 6.43 (d, J=9.9 Hz, 1H), 6.98 (d, J=2.1 Hz, 1H), 7.71 (d, J=2.2 Hz, 1H), 8.15 (d, J=9.9 Hz, 1H).

STEP 4: 5-[3-(Bis-2-chloroethyl)aminopropyloxy]methyl-8-methoxypsoralen or 5-[N,N,-Bis-(2-chloroethy)-3-aminopropoxy]methoxpsoralen (compound 4)

Thionyl chloride (0.040 mL, 0.55 mmol) was added dropwise to an ice bath chilled solution of 5-[3-(bis-2-hydroxyethyl)aminopropyloxyl]methyl-8-methoxypsoralen (10.0 mg, 0.0255 mmol) and pyridine (0.040 mL, 0.49 mmol) in $CH_2Cl_2$ (2mL). The reaction mix was covere d with a serum cap and allowed to stir 5 h at rt under nitrogen, then stripped under reduced vacuum and partitioned between $CH_2Cl_2$ and 10% $NaHCO_3$. The organic layer was washed several times with aqueous $NaHCO_3$, then brine. After drying with anhydrous $Na_2SO_4$, solvent was rotovapped off to give 5-[3-(bis-2-chloroethyl) aminopropyloxy]methyl-8-methoxypsoralen (0.0075 mg, 63.0% yield), as a syrup. $^1$H NMR ($CDCl_3$): d 1.71 (t, J=6.1 Hz, 2H), 2.60 (t, J=6.4 Hz, 2H), 2.82 (t, J=6.6 Hz, 4H), 3.3–3.7 (m, 6H), 4.29 (s, 3H), 4.86 (s, 2H), 6.43 (d, J=9.9 Hz, 1H), 6.96 (s, 1H), 7.71 (s, 1H), 8.15 (d, J=9.9 Hz, 1H).

EXAMPLE 21

This example describes the synthesis of 5'-[4-(Bis-2-chloroethyl)-amino-1-butylaminomethyl]-4,4',8-trimethylpsoralen (compound 16)

STEP 1: 5'-[4-(Bis-2-hydroxyethyl)amino-1-butylaminomethyl]-4,4',8-trimethylpsoralen A solution of 5'-b romomethyl-4,4',8-trimethylpsoralen (U.S. Pat. No. 4,294,822, 73.0 mg, 0.227 mmol), and N,N-bi s(2-hydroxyethyl)-1,4-butanediamine (400 mg, 2.27 mmol) were stirred in acetonitrile (100 mL) for 4 h. After rotovapping off the solvent, the resulting syrup was dissolved in $CH_2Cl_2$, washed with 0.3 M HCl several times, then chilled in an ice/water bath and made basic with powdered $K_2CO_3$. The product was extracted from the aqueous layer with several portions of $CH_2Cl_2$. The organic solution was rinsed with brine then dried with anhydrous $Na_2SO_4$ and stripped to give a brown syrup. The crude product was chromatographed by TLC (silica gel, 1/9 MeOH/$CHCl_3$) dissolved in $CH_2Cl_2$ to give 5'-[4-(bis-2-hydroxyethyl)amino-1-butylaminomethyl]-4,4',8-trimethylpsoralen, as a yellow syrup (26.9 mg, 29% yield). $^1$H NMR ($CDCl_3$): d 1.59 (s, 3H), 2.49–2.76 (m, 14H), 3.62 (t, J=5.3 Hz, 4H), 3.97 (s, 2H), 6.23 (d, J=1.1 Hz, 1H), 7.74 (s, 1H).

STEP 2: 5'-[4-(Bis-2-chloroethyl)amino-1-butylaminomethyl]-4,4',8-trimethylpsoralen or 4'-[4-(N,N-Bis-2-chloroethyl)aminobutoxy]methyl-4,5',8-trimethylpsoralen Thionyl chloride (0.020 mL, 0.278 mmol) was added dropwise to an ice bath chilled solution of 5'-[3-(bis-2-hydorxyethyl)amino-1-butylaminomethyl]-4,4',8-trimethylpsoralen (11.6 mg, 0.0278 mmol) and pyridine (0.023 mL, 0.278 mmol) in $CH_2Cl_2$ (5 mL). The reaction mix was covered with a serum cap and allowed to stir overnight at rt, then stripped under reduced vacuum and partitioned between $CH_2Cl_2$ and 10% $NaHCO_3$. The organic layer was washed several times with aqueous $NaHCO_3$, then brine. After drying with anhydrous $Na_2SO_4$, solvent was rotovapped off to give 5'-[4-(bis-2-chloroethyl)amino-1-butylaminomethyl]-4,4',8-trimethylpsoralen 5'-[4-(Bis-2-chloroethyl)-amino-1-butylaminomethyl]-4,4',8-trimethylpsoralen (9.3 mg, 73.8% yield), as a yellow solid. $^1$H NMR ($CDCl_3$): d 1.54 (m, 4H), 2.28 (s, 3H), 2.40–2.65 (m, 8H), 2.71 (t, J=6.8 Hz, 2H), 2.84 (t, J=7.0 Hz, 4H), 3.48 (t, J=7.0 Hz, 4 Hz), 3.97 (s, 2H), 6.24 (d, J=1.1 Hz, 1H), 7.47 (s, 1H).

5'-[5-(Bis-2-chloroethyl)amino-1-pentylaminomethyl]-4,4',8-trimethylpsoralen, (compound 17)

In the same manner as the foregoing, but using N,N-bis(2-hydroxyethyl)-1,5-pentanediamine in Step 1 in place of N,N-bis(2-hydroxyethyl)-1,4-butanediamine the title compound is produced.

5'-[6-(Bis-2-chloroethyl)amino-1-hexylaminomethyl]-4,4',8-trimethylpsoralen,(compound 18)

In the same manner as the foregoing, but using N,N-bis(2-hydroxyethyl)-1,6-hexanediamine in Step 1 in place of N,N-bis(2-hydroxyethyl)-1,4-butanediamine the title compound is produced.

4'-[3-(Bis-2-chloroethyl)amino-1-propylaminomethyl]-4,5',8-trimethylpsoralen, (compound 11)

In the same manner as the foregoing, but using 4'-bromomethyl-4,5',8-trimethylpsoralen (U.S. Pat. No. 4,124,598) and N,N-bis(2-hydroxyethyl)-1,3-prop anediamine in Step 1 in place of 5'-bromomethyl-4,4',8-trimethylpsoralen and N,N-bis(2-hydroxyethyl)-1,4-butanediamine respectively, the title compound is produced.

4'-[4-(Bis-2-chloroethyl)amino-1-butylaminomethyl]-4,5',8-trimethylpsoralen, (compound 12)

In the same manner as the foregoing, but using 4'-bromomethyl-4,5',8-trimethylpsoralen and N,N-bis(2-hydroxyethyl)-1,4-butanediamine in Step 1 in place of 5'-bromomethyl-4,4',8-trimethylpsoralen, the title compound is produced.

4'-[3-(Bis-2-chloroethy)amino-1-hexylaminomethyl]-4,5',8-trimethylpsoralen(compound 13)

In the same manner as the foregoing, but using 4'-bromomethyl-4,5',8-trimethylpsoralen and N,N-bis(2-hydroxyethyl)-1,6-hexanediamine in Step 1 in place of 5'-bromomethyl-4,4',8-trimethylpsoralen and N,N-bis (2-hydroxyethyl) 1,4-butanediamine respectively, the title compound is produced.

EXAMPLE 22

This example describes the synthesis of 4'-[4-(Bis-2-chloroethyl)aminobutoxy]methyl-4,5',8-trimethylpsoralen, (compound 9)

STEP 1: 4'-[(4-Methanesulfonyl)-butoxy]methyl-4,5',8-trimethylpsoralen

A solution of 4'-[(4-hydroxy)-butoxy]methyl-4,5',8-trimethylpsoralen(1-U.S. Pat. No. 4,269,852, 91.5 mg, 0.301 mmol) in $CH_2Cl_2$ (5 mL) was chilled with an ice/water bath. Triethylamine (0.14 mL, 1.00 mmol) then methanesulfonyl chloride (0.070 mL, 0.903 mmol) were added dropwise. The solution was allowed to warm to room temperature and stirred overnight. The reaction mixture was partitioned between $CH_2Cl_2$ and water. The organic layer was washed several times with aqueous $NaHCO_3$, then brine, and dried with anhydrous $Na_2SO_4$ and concentrated to give crude 4'-[(4-methanesulfonyl)-butoxy]methyl-4,5',8-trimethylpsoralen (0.106 g, 86.2% crude yield). $^1$H NMR ($CDCl_3$): d 1.71–1.86 (m, 4H), 2.47 (s, 6H), 2.52 (s, 3H), 2.95 (s, 3H), 3.51 (t, J=6.0, 2H), 4.21 (t, J=6.2, 2H), 4.59 (s, 2H), 6.20 (s, 1H), 7.54 (s, 1H).

STEP 2: 4'-[4-(Bis-2-hydroxyethyl)aminobutoxy]methyl-4,5',8-trimethylpsoralen

A solution of crude 4'-[(4-methanesulfonyl)-butoxy]methyl-4,5',8-trimethylpsoralen (106 mg, 0.260 mmol) and diethanolamine (300 mg, 2.85 mmol) were refluxed in acetonitrile (8 mL) overnight. After rotovapping off the solvent, the resulting syrup was dissolved in $CH_2Cl_2$, washed several times with aqueous $NaHCO_3$, then brine, and dried with anhydrous $Na_2SO_4$ and concentrated to give crude product which was chromatographed by TLC (silica gel, 95/5 $CHCl_3$-MeOH) to give a 4'-[4-(bis-2-hydroxyethyl)aminobutoxy]methyl-4,5',8-trimethylpsoralen as a yellow solid (32 mg, 27.1% yield). $^1$H NMR ($CDCl_3$): d 1.49–1.75 (m, 4H), 2.40–2.70 (m, 15H), 3.48 (t, J=5.8, 2H), 3.59 (t, J=5.3, 2H), 4.61 (s, 2H), 6.24 (d, J=1.1 Hz, 1H), 7.60 (s, 1H).

STEP 3: 4'-[4-(Bis-2-chloroethyl)aminobutoxy]methyl-4,5',8-trimethylpsoralen, (compound 9)

Thionyl chloride (0.040 mL, 0.55 mmol) was added dropwise to an ice bath chilled solution of 4'-[4-(bis-2-hydroxyethyl)aminobutyloxy]methyl-4,5',8-trimethylpsoralen (24.0 mg, 0.0575 mmol) and pyridine (0.050 mL, 0.62 mmol) in $CH_2Cl_2$ (3 mL). The reaction mix was covered with a serum cap and allowed to stir overnight at rt, then stripped under reduced vacuum and partitioned between $CH_2Cl_2$ and 10% $NaHCO_3$. The organic layer was washed several times with aqueous $NaHCO_3$, then brine. After drying with anhydrous $Na_2SO_4$, solvent was rotovapped off to give 4'-[4-(bis-2-chloroethyl)aminobutoxy]methyl-4,5',8-trimethylpsoralen (20.5 mg, 78.5% yield), as a yellow solid. $^1$H NMR (CDCl3): d 1.40–1.74 (m, 4H), 2.45–2.65 (m, 11H), 2.81 (t, J=7.0 Hz, 4H), 3.37–3.52 (m, 6H), 4.61 (s, 2H), 6.24 (s,1H), 7.59 (s, 1H).

It is to be understood that the present invention is not to be limited to the exact details of operation or exact compounds, compositions, methods, or procedures shown and described, as modifications and equivalents will be apparent to one skilled in the art. All patents described are hereby incorporated by reference.

EXAMPLE 23

TABLE 24

| Compound<br>M = N(CH₂CH₂Cl)₂<br>NA = not tested | Dose for<br>5 log kill<br>R-17 | Logs Virus Killed at Fixed Drug Dose | | | |
|---|---|---|---|---|---|
| | | R-17<br>0.5 μM | R-17<br>2 μM | R-17<br>5 μM | CA<br>HIV<br>15 μM |
| QM | ≦0.5 | >6 | >6 | >6 | 2.8–4.2 |
| 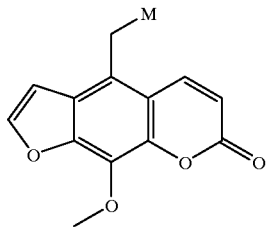<br>compound 2 | >30 | <0.5 | <0.5 | 0.5 | NA |
| 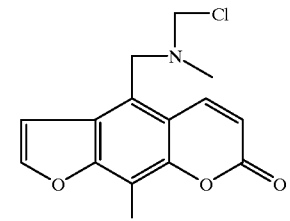<br>compound 3 | >75 | <0.5 | <0.5 | <0.5 | NA |
| 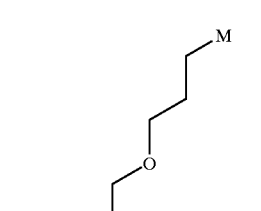<br>compound 4 | 12–25 | <0.5 | 0.5 | 2–3 | NA |
| 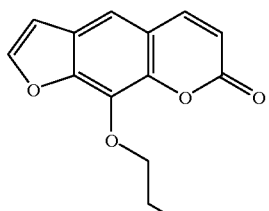<br>compound 5 | 10 | <0.5 | <0.5 | 2–3 | NA |

TABLE 24-continued

| Compound<br>M = N(CH₂CH₂Cl)₂<br>NA = not tested | Dose for<br>5 log kill<br>R-17 | Logs Virus Killed at Fixed Drug Dose | | | |
|---|---|---|---|---|---|
| | | R-17<br>0.5 μM | R-17<br>2 μM | R-17<br>5 μM | CA<br>HIV<br>15 μM |
| compound 6 | >30 | <0.5 | <0.5 | 1 | NA |

TABLE 25

| Compound | Dose for<br>5 log kill<br>(μM) | Logs Virus Killed at Fixed Drug Dose | | | |
|---|---|---|---|---|---|
| compound 7 | 2 | 2 | 5 | >6 | 0 |
| compound 8 | 7 | ? | 3 | 4 | 0.2 |
| compound 9 | NA | NA | NA | NA | NA |

TABLE 25-continued

| Compound | Dose for 5 log kill (μM) | Logs Virus Killed at Fixed Drug Dose | | | |
|---|---|---|---|---|---|
| M = N(CH$_2$CH$_2$Cl)$_2$<br>NA = not tested | R-17 | R-17<br>0.5 μM | R-17<br>2 μM | R-17<br>5 μM | CA-<br>HIV<br>15 μM |

TABLE 26

| Compound | Dose for 5 log kill (μM) | Logs Virus Killed at Fixed Drug Dose | | | |
|---|---|---|---|---|---|
| compound 10 | >30 | 0.5 | | | NA |
| compound 11, n = 3 | ≦2 | 1 | 6 | >6 | 0.4 |
| n = 4 S-210 | | | | | 0.8 |
| compound 13, n = 6 | ≦2 | ? | >6 | >6 | 1.5 |
| compound 14 | | | | | 1.0 |
| compound 15, n = 3 | | | | | 0.3 |

TABLE 26-continued

| Compound | Dose for 5 log kill (μM) | Logs Virus Killed at Fixed Drug Dose | | | |
|---|---|---|---|---|---|
| | | R-17 | R-17 0.5 μM | R-17 2 μM | R-1'7 5 μM | CA-HIV 15 μM |
| M = N(CH$_2$CH$_2$Cl)$_2$ NA = not tested | | | | | |

TABLE 27

| Compound[a] | Dose for 5 log kill (μM) R-17 | Logs Virus Killed at Fixed Drug Dose | | | |
|---|---|---|---|---|---|
| | | R-17 0.5 μM | R-17 2 μM | R-1'7 5 μM | CA-HIV 15 μM |
| (structure shown below) | ≦2 | ? | >6 | >6 | 0.7 |

M(CH$_2$)$_n$NH—[furocoumarin structure]

n = 4 compound 16 n = 5 compound 17
n = 6 compound 18

We claim:

1. An in vitro method of treating mammalian blood or a blood product to inactivate a viral, bacterial or protozoan pathogen, the method comprising:
   (a) contacting in vitro a mammalian blood or blood product with a viral, bacterial or protozoan pathogen inactivating amount of a compound I, wherein,
      (i) compound I has an intercalator nucleic acid binding ligand and a mustard group attached thereto, and
      (ii) compound I when incubated with a composition comprising a blood product containing R17, has a greater inactivation efficiency against R17 than a compound II containing a mustard group that lacks the intercalator nucleic acid binding ligand, and
      (iii) the treating with the pathogen inactivating amount of Compound I results in the inactivation of at least 1 log of pathogen present in the blood or blood product, if any; and
   (b) recovering the pathogen inactivated mammalian blood or blood product, wherein the recovered product has substantially the same biological activity such that it is suitable for therapeutic use in a mammal.

2. The method according to claim 1 wherein the pathogen is a RNA-containing virus.

3. The method according to claim 2 wherein the pathogen is HIV.

4. The method according to claim 1 wherein the pathogen is a DNA-containing virus.

5. The method according to claim 4 wherein the pathogen is a hepatitis virus.

6. The method according to claim 1, wherein the contacting in vitro is for a time between 1 minute and 48 hours.

7. The method according to claim 1, wherein compound I is present at a concentration of 320 micromolar or less.

8. The method of claim 1, further comprising:
   c) removing said compound I from said blood or blood product with an adsorbent material.

9. The method of claim 8, further comprising:
   d) transfusing the recovered product into a mammal.

10. A method according to claim 1, wherein the nucleic binding ligand is an acridine.

11. The method according to claim 10, wherein the acridine is 9-aminoacridine.

12. The method according to claim 10, wherein the compound is [N-(2-chloroethlyl)-N-ethyl-N'-(6-chloro-2-methoxy-9-acrdinyl)-1,3-propanediamine dihydrochloride] N-(2-chloroethyl)-N-ethyl-N'-(6-chloro-2-methoxy-9-acridinyl)-1,3-propanediamine dihydrochloride.

13. The method according to claim 11, wherein the nucleic binding ligand is a psoralen.

14. The method according to any one of claims 1–13, wherein the blood product is comprised of red blood cells.

15. The method according to any one of claims 1–13, wherein the blood product is comprised of platelets.

16. The method according to any one of claims 1–13, wherein the blood product is comprised of plasma.

17. The method according to any one of claims 1–13, wherein the treatment is of whole blood.

18. The method of claim 14 wherein the mammal is a human.

19. The method of claim 15 wherein the mammal is a human.

20. The method of claim 16 wherein the mammal is a human.

21. The method of claim 17 wherein the mammal is a human.

* * * * *